United States Patent [19]

Bhasin

[11] Patent Number: 4,908,343
[45] Date of Patent: Mar. 13, 1990

[54] CATALYST COMPOSITION FOR OXIDATION OF ETHYLENE TO ETHYLENE OXIDE

[75] Inventor: Madan M. Bhasin, Charleston, W. Va.

[73] Assignee: Union Carbide Chemicals and Plastics Company Inc., Danbury, Conn.

[21] Appl. No.: 251,573

[22] Filed: Oct. 3, 1988

Related U.S. Application Data

[63] Continuation-in-part of Ser. No. 18,809, Feb. 20, 1987, abandoned, which is a continuation of Ser. No. 640,269, Aug. 13, 1984, abandoned.

[51] Int. Cl.$^4$ .................. B01J 23/02; B01J 23/04; B01J 23/50
[52] U.S. Cl. .................... 502/218; 502/208; 502/317; 502/324; 502/340; 502/341; 502/347; 502/348; 549/536
[58] Field of Search .............. 502/208, 218, 317, 324, 502/340, 341, 347, 348; 549/536

[56] References Cited

U.S. PATENT DOCUMENTS

| | | | |
|---|---|---|---|
| 4,123,385 | 10/1978 | Rebsdat et al. | 502/348 X |
| 4,389,338 | 6/1983 | Mitsuhata et al. | 502/348 |
| 4,458,032 | 7/1984 | Rebsdat et al. | 502/347 X |
| 4,471,071 | 9/1984 | Rebsdat et al. | 502/348 X |
| 4,761,394 | 8/1988 | Lauritzen | 502/348 |
| 4,808,738 | 2/1989 | Lauritzen | 549/536 |
| 4,820,675 | 4/1989 | Lauritzen | 502/216 |

FOREIGN PATENT DOCUMENTS

| | | |
|---|---|---|
| 0247414 | 2/1987 | European Pat. Off. . |
| 0266015 | 4/1988 | European Pat. Off. . |
| 0266852 | 11/1988 | European Pat. Off. . |
| 56-105750 | 8/1981 | Japan . |
| 57-21937 | 2/1982 | Japan . |
| 2043481 | 10/1980 | United Kingdom . |

OTHER PUBLICATIONS

Above References Were Cited in Parent Application SN 18,809.

Primary Examiner—W. J. Shine
Attorney, Agent, or Firm—Morris N. Reinisch

[57] ABSTRACT

This invention relates to catalysts for the manufacture of ethylene oxide, especially at commercial concentrations in the presence of carbon dioxide gas recycle, which contains impregnated silver on a support and a mixture of cesium salt and one or more alkali metal and alkaline earth metal salts in which the anions thereof are halide or oxyanions of elements other than the oxygen therein having an atomic number of 7 or 15 to 83 and being from groups 3b through 7b, inclusive, and 3a through 7a, inclusive, of the Periodic Table of the Elements, at least a portion of said oxyanions are oxyanions of group 3b to 7b elements.

44 Claims, No Drawings

CATALYST COMPOSITION FOR OXIDATION OF ETHYLENE TO ETHYLENE OXIDE

This is a continuation-in-part of U.S. Ser. No. 18,809, filed Feb. 20, 1987, now abandoned, which is a continuation of U.S. Ser. No. 640,269, filed Aug. 13, 1984, now abandoned, both of which are herein incorporated by reference. This application is related to U.S. Ser. No. 251,814, filed on even date herewith.

BRIEF SUMMARY OF THE INVENTION

TECHNICAL FIELD

This invention relates to catalysts for the manufacture of ethylene oxide especially at commercial concentrations in the presence of carbon dioxide gas recycle, which contain impregnated silver on a support, e.g., an alpha-alumina support having an alpha-alumina content (inclusive of binder) of at least 98 percent (98%) by weight, and a mixture of (a) at least one cesium salt and (b) one or more alkali metal and alkaline earth metal salts of lithium, sodium, potassium, rubidium, magnesium, calcium, strontiun and barium, said mixture comprising (i) a cesium salt of an element other than the oxygen therein being selected from groups 3b through 7b, inclusive, of the Periodic Table of the Elements, and (ii) alkali metal and/or alkaline earth metal salt in which the anions of such salt comprise at least one of halide of atomic numbers of 9 to 53, inclusive, and oxyanions of elements other than the oxygen therein having an atomic number of 7 or 15 to 83, inclusive, and selected from the groups 3a to 7a, inclusive, and 3b to 7b, inclusive, of the Periodic Table of the Elements. The mixture is preferably in an amount sufficient to provide an efficiency to ethylene oxide manufacture at a value at least about 79 percent, as determined at STANDARD ETHYLENE OXIDE PROCESS CONDITIONS measured under oxygen process conditions. There is also described herein a process of making such catalysts and processes for producing ethylene oxide with such catalysts.

BACKGROUND ART

Introduction

This invention is concerned in general with silver catalysts, their manufacture and their use in the manufacture of ethylene oxide in commercial concentrations in the presence of a gas phase inhibitor, especially a gas phase chloride inhibitor, and advantageously carbon dioxide recycle. The catalyst of this invention comprises a supported silver catalyst. The catalyst contains cesium salts of an oxyanion in combination with at least one other alkali metal and/or alkaline earth metal salt of a halide or an oxyanion. Preferably, another alkali metal is present and is lithium, sodium, potassium and/or rubidium. The oxyanions contain elements other than the oxygen therein having an atomic number of 7 or 15 to 83, inclusive, and being from the groups 3b, through 7b, inclusive, and 3a through 7a, inclusive, of the Periodic Table of the Elements. Thus, the catalyst, when utilized in the manufacture of ethylene oxide, contains a select class of salts of cesium with one or more other select classes of salts of other alkali metals (excluding francium) and alkaline earth metals. The amount of these salts employed is not governed by prior art notions of weight or volume percentages because, as will be explained herein, such factors cease in general to be relevant. Thus, this invention allows the use of amounts of alkali metals and alkaline earth metals which cover a broad range to yield catalysts having desirable performances.

SUMMARY ANALYSIS OF PRIOR ART

In order to understand and appreciate this invention, it is desirable to review some basic facts about the science of making ethylene oxide by the gas phase reaction of ethylene and oxygen over a solid silver catalyst.

A number of theories abound about the mechanism of the reaction of ethylene and oxygen. It is sufficient to say that none is universally accepted. What appears to be accepted is that oxygen in some fashion combines with solid silver and through that combination, oxygen is caused to react with ethylene to form ethylene oxide. Concomitant with that reaction is the combustion of ethylene and/or ethylene oxide to carbon dioxide and water (combustion products). Some have theorized that at least a portion of the carbon dioxide is generated by the isomerization of ethylene oxide to acetaldehyde which immediately goes to combustion products.

It is these competing reactions that the workers in the art attempt to affect. Many additives have been used to enhance the reaction. To illustrate this point, it must be recognized that the best procedures employed today to make commercial silver catalysts when used to make a silver only catalyst, i.e., silver impregnated on a porous alpha-alumina support, will result in a catalyst which, under commercial ethylene oxide process conditions (exclusive of gas phase inhibitor addition), generates at best a selectivity or efficiency to ethylene oxide of about 35–50%, and reduced catalytic activity. The most significant contributor to improving selectivity or efficiency and activity is the addition of gas phase organic chloride compounds such as ethyl chloride, ethylene dichloride and vinyl chloride. Many other gas phase additives to enhance selectivity have been depicted in the art (See Law, et al., U.S. Pat. Nos. 2,279,469 and 2,279,470) and they range from the addition of nitrogen oxides, ammonia to xylene. All of them, at one time or another, have been found to beneficially affect efficiency.

Another class of additives are those incorporated into the silver catalyst and are not part of the gas phase fed or provided to the catalyst. There are many metals which when added into the silver catalyst beneficially affect the performance of the catalyst. Some say that they act as promoters and others attribute the benefit to an inhibiting or suppressing action. In the absence of the gas phase additives, these metals make little contribution, if any, to the catalyst's performance. However, in the presence of the gas phase additive, the net effect is an improvement in the amount of ethylene oxide produced and a concomitant reduction in carbon dioxide. Such metals cover the spectrum of the Periodic Table and their roles in the reaction are not understood at this time. Presently, certain of the alkali metals have found favor as additives for enhancing performance of the silver catalysts. This subject will be readdressed later.

Though metals have received much attention relatively little attention in the literature has been given to the role of anions in this reaction. Silver salts such as silver nitrate, silver lactate and silver oxalate have long been used as a source of silver metal. Since the silver salts are reduced by roasting to the metal form, their selection would appear to have been arbitrary except when those salts deposit or occlude contaminating cations. Of course, the silver salts employed should have sufficient solubility in the solvating medium to effect the deposition of desired amounts of silver metal on the catalyst. For example, the manufacture of silver oxalate by the reaction of silver nitrate with potassium oxalate leaves behind in the silver oxalate a small amount of potassium which cannot be removed from the silver oxalate and it goes along for a ride with the silver in the remainder of the catalyst preparation steps. This is classically demonstrated in carrying out the processes of examples I and II F of U.S. Pat. No. 3,702,259. As it turns out, the amount of potassium occluded is sufficient to yield the beneficial results according to that patent of enhanced selectivity and activity (see, in addition, the Nielsen and LaRochelle U.S. Pat. Nos. 3,962,136, 4,012,425, 4,010,115 and 4,356,312, part of a later series of patents which attribute selectivity gains to usage of relatively narrow amounts of the alkali metals potassium, rubidium or cesium). The manner in which silver is provided in the support (or carrier), with the exception of the erroneous conceptions of U.S. Pat. No. 3,702,259, seems not to be important except for one point. If the support contains a lot of leachable impurities, the acidity or basicity of the medium out of which the silver is deposited should not be so strong as to leach them from the support and become part of the silver catalyst in amounts to adversely affect the performance of the catalyst in the ethylene oxide reaction. However, if one wishes to employ such leachates to enhance the performance of the catalyst, then, of course, the leaching action is desirable.

Some early references in the art have suggested the use of alkali metal halide (see Gould, Sears, Brengle, et al., and Sacken, infra) but they seemed to be more interested in providing a process for adding both alkali, the promoter, and chloride the inhibitor, to accommodate the known benefits of alkali promotion and chlorine inhibition, see Law, et al., supra. and Evans, infra. By the time of their work Law, et al., had already proven in commercial operations that gas phase chloride addition was a significant contributor to enhanced production of ethylene oxide. The role of chlorine or chloride was easily speculated about because of silver's known propensity for reaction with chlorine to form silver chloride. Whether right or wrong, it became and still is fashionable to presume that surface silver chloride plays some role in either achieving or controlling the reaction. Indeed, the concept that the alkali metals remain as salts in the silver catalyst after manufacture seems in some quarters to be unthinkable, see the aforementioned Nielsen and LaRochelle patents, where the alkali metal is perceived to be in its final form as the oxide. As a matter of fact the process of Nielsen 3,702,259 serves to convert the occluded potassium into its nitrate salt as shown by Nielsen and Schroer, Belgium Patent 779,699. The belief that such alkali metal addition converted the alkali to the oxide is also found in De Krijger and Wattimina U.S. Pat. No. 3,563,923, who added lithium compounds to the support prior to silver deposition. Rightly or wrongly, the authors thought the lithium went to the oxide form. We believe those positions are incorrect and that the alkali metals always form salts, either as the salts as deposited, or formed in situ either with the support (or the binder portion of the support) or formed in situ during catalyst manufacture (see Nielsen and Schroer, supra) or later converted during use by reaction with gas phase components which provides anions such as nitrate, chloride and/or carbonate.

As viewed by the prior art, the role of alkali metal was presumed to provide a promoter component and, with the exception of when the halide salt was described for providing halide inhibition, the role of anion has been regarded to be unimportant. One exception is Sacken, U.S. Pat. No. 2,671,764, who describes, the benefits derived from the provision of alkali metal sulfates. [This patent will hereinafter be called the "Sacken sulfate" patent to distinguish it from U.S. Pat. No. 2,765,283, in which Sacken employs alkali metal halide additive.] Unquestionably, the Sacken sulfate patent recognizes benefits from the use of alkali metal sulfate as promoters for the silver catalyzed ethylene oxide reaction. However, the Sacken sulfate patent practices the process in the absence of gas phase inhibitor such as organic chlorides. Consequently, the results depicted in the patent is a process which yields a low ethylene oxide selectivity. Even though the Sacken sulfate patent specifies the use of alkali metal sulfate, it is only compared with the corresponding hydroxide in showing that the sulfate anion plays a role in the ethylene oxide reaction. The prime variable in the Sacken sulfate patent appears to be the choice of alkali metal. Other exceptions are U.S. Pat. Nos. 4,414,135 and 4,415,476, in which the first patent proposes the use of cesium bromide or fluoride and the second patent proposes the use of more than 1000 ppm of sodium and cesium, both as their chlorides (compare U.K. Patent 2,043,481, page 18, Table VI). The last exception is U.S. Pat. No. 4,406,820 which employs certain alkali metal salts of organic acids such as m-hydroxy-benzoic acid and acrylic acid. Such anions would be expected to be converted to combustion products.

The successful commercial employment of ethylene oxide catalysts depends in part upon a variety of factors other than the efficiency or selectivity and activity issues emphasized so frequently in the literature (especially the patent literature). Laboratory experimentations in this field run the gamut from testing and evaluating such catalysts in microreactors (i.e., tiny tubular reactors for testing crushed catalyst particles) to backmixed autoclaves of the Berty type (i.e., larger reactors which test full sized catalyst pellets and generally employ full gas recycle). Microreactors can yield the highest efficiency numbers, typically far greater than is obtainable in commercial tubular reactor operations for the same catalyst in non crushed condition, while backmixed autoclaves typically provide the lowest efficiency numbers because the entire catalyst is exposed to the outlet gas which has the lowest concentration of reactants and the highest concentration of products. Thus, direct comparisons between such reactor systems are not easily obtainable. Catalyst efficiency can be enhanced by a number of tricks such as by using unusually high amounts of ethylene or oxygen in the feed gas, low reaction rates, manipulation of inhibitor content in the gas feed, and by the reduction or elimination of carbon dioxide in the gas feed. Consequently, allegations of superiority or desirability of one catalyst over another have to be tested in controlled and comparable ways. But given that a catalyst provides under controlled and comparable conditions superior efficiency (or selectivity) values over another catalyst, such would be meaningless in the commercial world unless that superiority in performance is obtainable in respect to a commercially-usable catalyst size, a commercial size charge of such catalyst and such catalyst charge has respectable aging characteristics during commercial usage. Moreover, the catalyst should commercial usage has to satisfy a number of requirements. It must have a physical form and strength to allow proper gas flow in the reactor without being crushed. Catalyst breakage or abrasion is essentially unacceptable because of the pressure drop ad safety problems created. The catalyst should be able to withstand a certain amount of temperature rise in the reactor, and be regenerable when over chlorinated, which can and usually does happen on occasion during a catalyst's life in a commercial operation. It is desirable that an ethylene oxide catalyst be resistant to feed contaminations and regenerable when poisoned by inadvertent discharge of agueous caustic into the catalyst beds. Thus what may be an improvement in catalysis by one standard may be meaningless if the catalyst fails the other important characteristics and properties, and what may seem to be a highly efficient catalyst may only be so because of the method used to define such efficiency.

DETAILED DISCUSSION OF PRIOR ART

The manufacture of ethylene oxide by the reaction of oxygen or oxygen-containing gases with ethylene in the presence of a silver catalyst is an old and developed art. For example, U. S. Pat. No. 2,040,782, patented May 12, 1936, describes the manufacture of ethylene oxide by the reaction of oxygen with ethylene in the presence of silver catalysts which contain a class of metal promoters. In Reissue U. S. Pat. No. 20,370, dated May 18, 1937, Leforte discloses that the formation of olefin oxides may be effected by causing olefins to combine directly with molecular oxygen in the presence of a silver catalyst. From that point on, the prior art has focused its efforts on improving the catalyst's efficiency in producing ethylene oxide.

In characterizing this invention, the terms "conversion", "selectivity", and "yield" are employed as defined in U. S. Pat. No. 3,420,784, patented Jan. 7, 1969, at column 3, lines 24-35 inclusive. This definition of "selectivity" is consistent with that disclosed in U. S. Pat. No. 2,766,261 at column 6, lines 5-22, and U. S. Pat. No. 3,144,916, lines 58-61. The definitions of "yield" and "conversion" have more varied meaning in the art and are not to be employed as defined, for example, in the aforementioned U. S. Pat. No. 2,766,261. The terms "efficiency" and "selectivity", as used throughout the specification and claims are intended to be synonomous.

Silver catalysts employed in the manufacture of ethylene oxide have undergone significant changes since their initial period of development. As reported by the art, silver particles were first deposited upon support materials with little attention being paid to support properties, such as surface area, pore volume and chemical inertness. As the art evolved, there developed special technologies related to carriers or supports containing silver that were more effective for the reaction of ethylene with oxygen to produce ethylene oxide. Today, most supports for the silver catalysts are shaped particulate materials which can be loaded in the interior of a reactor wherein the reacting gases and the gaseous products of the reaction are capable of flowing in and about these particulate materials to pass through the reactor and be recovered. The size and shape of the support are variable factors and the particular size and shape selected are peculiar to the reactor employed, the gas flow required, and the pressure drop across the reactor, with other factors also being considered.

The carriers that have been employed are typically made of inorganic materials, generally of a mineral nature. In most cases, the preferred carrier is made of alpha-alumina, such as has been described in the patent literature: see for example, U. S. Pat. Nos. 2,294,383; 3,172,893; 3,332,887; 3,423,328; and 3,563,914.

The carriers which are employed for the manufacture of most, if not all, commercially employed ethylene oxide catalysts are produced by companies who do not produce such catalysts. As a rule, the methods of making such carriers are trade secrets of significant value to the carrier manufacturers. Consequently, the catalyst manufacturer cannot know how the carrier is made. Critical to making a carrier which proves uniquely desirable for the manufacture of a successful catalyst can be a number of factors, such as the purity and other physical/chemical properties of raw materials used to make the carrier and the method by which the carrier is made.

The silver that is deposited on these carriers is thought to be in the form of small particles because that is all that can be seen by current microscopic techniques. The patent literature indicates that the size of the silver is a factor in the effectiveness of the catalyst and in most cases fine particle silver is obtained utilizing the standard processes in the art; see, for example, U. S. Pat. Nos. 2,554,459; 2,831,870; 3,423,328 (specifies that silver particles of 150-400 Angstroms are employed): 3,702,259 (disclosed a preparation procedure for forming silver particles less than 1 micron in diameter) and 3,758,418 (discloses silver particles having a diameter less than 1000 Angstroms). Improvements in microscopic examinations of silver catalysts enable the observation that the particle size ranges to even smaller values.

The deposition of silver onto the carrier can be achieved by a number of techniques but the two techniques which are most frequently employed involve, in one case, the impregnation of the support with a silver solution followed by heat treatment of the impregnated support to effect deposition of the silver on the support and in the other case, the coating of the silver on the support by the precipitation of silver or the preformation of silver into a slurry such that the silver particles are deposited on the support and adhere to the support surface when the carrier or support is heated to remove the liquids present. These various procedures are exemplified in various U. S. Pat. Nos. such as 2,773,844; 3,207,700; 3,501,407; 3,664,970 (see British Patent 754,593) and 3,172,893.

The surface area provided by the support has been the subject of considerable interest in the development of silver catalysts. Disclosures concerning the surface area of the catalyst carrier can be found in U. S. Pat. No. 2,766,261 (which discloses that a surface area of 0.002-10 m2/gm is suitable); U. S. Pat. No. 3,172,893 which depicts a porosity of 35-65% and a pore diameter of 80-200 microns); U. S. Pat. No. 3,725,307 which depicts a surface area of less than 1 sg.m/gm and an average pore diameter of 10-15 microns): U. S. Pat. No. 3,664,970 (which utilizes a support having a minimum porosity of about 30%, at least 90% of the pores having diameters in the range of 1-30 microns, and the average of such diameters being in the range of 4-10 microns); and U. S. Pat. No. 3,563,914 which utilizes a catalyst support having a surface area of less than 1 sg. m/gm, a volume of 0.23 ml/gm and a particle size between 0.074 and 0.30 mm). Low surface area, inert alpha alumina is favored by the prior art.

· As mentioned above, the workers in the field have determined that a variety of metals or metal cations when present in combination with the silver could act to promote a silver catalyst's ability to make ethylene oxide. These materials in themselves are not considered catalysts. Their presence in the catalyst has appeared to contribute to enhancing the rate or amount of oxide production but, as pointed out above, that contribution generally depends upon the presence of a gas phase additive such as the so-called gas phase inhibitor. Because the competing reactions in the reactor occur simultaneously and the critical factor in determining the effectiveness of the overall process is the measure of control one has over these competing reactions, inevitably a material which enhances the production of ethylene oxide might also be considered a material which inhibits the complete combustion of ethylene to carbon dioxide and water. Thus, there is a problem in defining whether that material which is termed a promoter is in fact an inhibitor of the combustion reaction. Where gas phase inhibitors are present and a so called promoted catalyst is used, a co action occurs which leaves one to question whether the "promoter" materials are in reality inhibitors or promoters. However, this matter seems to be an irrelevant issue. What is significant is that the outcome of the reaction is favorable to the efficient production of ethylene oxide.

It has been known for a long time that impurities present in the catalyst and/or the gas phase can materially impact upon the reaction. In the early development of the art, there were no techniques available for identifying or measuring such impurities. Consequently, one could not isolate the role that such impurities played However, even in the earliest periods of the development of the art, the use of alkali metals as promoters for the silver catalyzed production of ethylene oxide was extremely well known in the art. U.S. Pat. No. 2,177,361, issued October 1939, has a teaching of the use of alkali metals in silver catalysts. U.S. Pat. No. 2,238,471 discloses that lithium is very desirable as a promoter but that potassium and cesium are detrimental when used in amounts of essentially 10% by weight of potassium hydroxide or cesium hydroxide to the silver oxide employed in making the catalyst. Later, U.S. Pat. No. 2,404,438 states that sodium and lithium are effective promoters for this reaction. Essentially the same teaching can be found in U.S. Pat. No. 2,424,084. U.S. Pat. No. 2,424,086 generalizes about alkali metals as promoters and specifies sodium in particular. In U.S. Pat. No. 2,671,764 (the Sacken sulfate patent), the patentees believe that alkali metals in the form of their sulfates are effective as promoters for such silver catalysts. In particular, the patentees state that sodium, potassium, lithium, rubidium or cesium sulfates may be used as promoters. U.S. Pat. No. 2,765,283 describes the pretreatment of a support with a dilute solution of a chlorine containing compound and indicates that such chlorine compounds should be inorganic. Particular illustrations cited of suitable inorganic chlorine compounds included sodium chloride, lithium chloride and potassium chlorate. This patent specifies that the amount of the inorganic chlorine containing compound which is deposited on the catalyst support is from 0.0001% to 0.2% by weight, based on the weight of the support. U.S. Pat. No. 2,615,900 to Sears describes the use of metal halide in the treatment of the supported catalyst and specifies that such halides can be of alkali metals such as lithium, sodium, potassium and cesium. The metal halide is present in the range of 0.01% to 50% based upon the weight of metallic silver. The patent also specifies that mixtures of the individual metal halides generally classified in the patent may be used to advantage to enhance the break-in period of a new catalyst composition while at the same time maintaining a moderate but steady activity of the catalyst over an extended period of time during normal operation. Thus, one particular metal halide treated catalyst would provide a short term high initial activity whereas another of the metal halides would provide a longer term moderate activity for the catalyst. This patent takes the position that the metal halides which are provided in the catalyst serve to inhibit the combustion of ethylene to carbon dioxide and thus classifies these materials as catalyst depressants or anticatalytic materials. U.S. Pat. No. 2,709,173 describes the use of a silver catalyst for making ethylene oxide in which there are provided simultaneously with the introduction of silver to the solid support, any of the alkali metal halides such as lithium, sodium, potassium, and rubidium compounds of chlorine, bromine and iodine, to enhance the overall production of ethylene oxide. The patent specifies small amounts "of less than about 0.5% are desirable". In particular, the patent emphasizes "proportions of alkali metal halide within the range of about 0.0001 to about 0.1%" are most preferred. The patent states that "although the preferred catalyst composition contains a separate promoter it is not always necessary since during preparation of the catalyst the alkali metal halide may be converted to some extent to the corresponding alkali metal oxide which acts as a promoter." U.S. Pat. No. 2,766,261 appears to draw from the teachings of U.S. Pat. No. 2,238,474 in that cesium and potassium are said to be detrimental in silver catalysts; sodium and lithium are suggested as useful promoters. However, U.S. Pat. No. 2,769,016 finds that sodium, potassium and lithium are promoters when used in the silver catalysts. This latter patent also recommends the pretreatment of the support with dilute solutions of sodium chloride, lithium chloride or potassium chlorate. U.S. Pat. No. 2,799,687 to Gould, et al., states that the addition of metal halides within the range described by Sears in U.S. Pat. No. 2,615,900 is not productive of optimum results. This is said to be especially true in the case of alkali metal halides, particularly the chloride and fluoride of sodium and potassium. The patentees recommend that the inorganic halide component of the catalyst be maintained within the range of 0.01-5 weight percent, preferably 0.01 to 0.1 weight percent, based on the weight of the "silver oxidative catalytic component," i.e., the silver salt transformed into elemental silver. U.S. Pat. No. 3,144,416 mentions a variety of metals as promoters and one of them is cesium. U.S. Pat. No. 3,258,433 indicates that sodium is an effective promoter. U.S. Pat. No. 3,563,913 recommends the use of alkali metals such as lithium compounds as promoters. The preferred amount of promoting material is said to be about 0.03 to 0.5%, by weight of metal oxide based on the weight of the support. U.S. Pat. No. 3,585,217 states that alkali metal chlorides "are known to counteract the formation of carbon dioxide" and "may be incorporated into the catalyst". U.S. Pat. No. 3,125,538 discloses a supported silver catalyst containing a coincidentally deposited alkali metal selected from among potassium, rubidium and cesium in a specified gram atom ratio relative to silver. The weight of silver is preferably 2-5%, by weight, of the catalyst. The patentees characterize this catalyst as being especially suitable for the reaction of nitric oxide with propylene. This same catalyst is produced inherently by the processes of the examples of U.S. Pat. No. 3,702,259, as discussed previously, which patent promotes their use for making ethylene oxide. U.S. Pat. Nos. 3,962,136 and 4,012,425 also disclose that same catalyst as being useful for ethylene oxide production. U.S. Pat. No. 3,962,136 describes the coincidental deposition of alkali metal with the silver on the support, the alkali metals being present in their final form on the support in the form of an oxide in which the oxide consists of cesium, rubidium or mixtures of both, optionally, combined with a minor amount of an oxide of potassium. The amount of such oxide is from about $4.0 \times 10^{-5}$ gew/kg to about $8.0 \times 10^{-3}$ gew/kg of total catalyst. However, U.S. Pat. No. 4,010,115, patented Mar. 1, 1977, purports to distinguish itself from the other patents by employing as the oxide of the alkali metal the oxide of potassium optionally combined with a minor amount of an oxide of rubidium or cesium. U.S. Pat. No. 4,356,312 describes the use of the same catalyst. Application Ser. No. 317,349, filed Dec. 21, 1972, which is a parent to U.S. Pat. Nos. 3,962,136 and 4,010,115, and others, contains some interesting data deserving of comment. According to example 2 which contains some comparative experiments, there is described the manufacture of a catalyst which contains 310 parts per million by weight of coincidentally-added potassium and that catalyst when employed as an ethylene oxidation catalyst was found to be inactive for the production of ethylene oxide.

U.S. Pat. No. 4,207,210 (corres. Belgium Patent 821,439, based upon British Patent Specification 1,489,335) discloses that a catalyst can be made that is equivalent to that produced in the so-called parent applications cited in U.S. Pat. Nos. 3,962,136, 4,012,425, and Patent 4,010,115 by using a sequential procedure by which the alkali metal is supplied to the support. Thus, the criticality in the method of deposition of alkali metal in the catalyst appears doubtful in the face of that type of disclosure and the disclosure of U.S. Pat. Nos. 4,033,903 and 4,125,480 which describe subjecting used silver-containing catalysts to a post-addition of one or more of potassium, rubidium or cesium. Apparently such treatment regenerates the catalyst's ability to enhance selectivity to ethylene oxide. Another patent which tends to indicate that a post addition of alkali metal such as cesium gives results equivalent to either pre-addition or simultaneous addition is U.S. Pat. No. 4,066,575.

German Offenlegungsschrift 2,640,540 discloses in its examples a silver catalyst for ethylene oxide production containing sodium and either potassium, rubidium or cesium.

Japanese Application Publication Disclosure No. 95213/75 is directed to a process for producing ethylene oxide using a catalyst composition comprising silver, barium, potassium and cesium in specified atomic ratios. Table I of this disclosure summarizes the efficiencies achieved with the various catalyst compositions of the examples.

U.S. Pat. No. 4,039,561 discloses a catalyst for preparing ethylene oxide containing silver, tin, antimony, thallium, potassium, cesium and oxygen in specified atomic ratios.

Belgium Patent 854,904 discloses silver catalysts containing various mixtures of sodium and cesium. U.K. Patent Application 2,002,252 discloses, in Table 2, supported silver catalysts containing various mixtures of cesium and thallium, some of which additionally contain potassium or antimony. U.S. Pat. No. 4,007,135 broadly discloses (in column 2, lines 25-30) silver catalysts for alkylene oxide production containing silver "together with a promoting amount of at least one promoter selected from lithium, potassium, sodium, rubidium, cesium, copper, gold, magnesium, zinc, cadmium, strontium, calcium, niobium, tantalum, molybdenum, tungsten, chromium, vanadium and barium...". U. S. Pat. Nos. 3,844,981 and 3,962,285 disclose catalysts and processes for epoxidizing olefins in the presence of a multimetallic component. The catalyst in the 3,962,285 patent is said to comprise a minor amount of one or more of palladium, uthenium, rhenium, iron and platinum with a major amount of silver. The 3,844,981 patent discloses the preparation of the catalyst from a decomposible salt of group 7b, 1b or the iron group of group 8 of the Periodic Table of the Elements. Preferably, the salt is selected from the group of gold, copper, rhenium, manganese and iron salts. While the patentee contemplates that these metals are in the metallic state, oxidation during epoxidation conditions may occur with one or more of these metals, e.g., rhenium, to form oxyanions containing the metal.

European Patent Publication No. 0003642 discloses, in Table 3, silver containing catalysts which include mixtures of potassium and cesium, and a catalyst containing sodium and cesium.

Belgium Patent 867,045 discloses supported silver catalysts containing what is referred to as an effective proportion of lithium and a substantially lesser amount of alkali metal selected from among cesium, rubidium and/or potassium.

Belgium Patent 867,185 discloses supported silver catalysts for ethylene oxide production containing a specified amount of potassium and at least one other alkali metal selected from rubidium and cesium.

United Kingdom Patent No. 2,043,481, commonly assigned, describes the use of a synergistic combination of cesium and at least one other alkali metal in combination with silver on an inert support to provide catalysts which were superior to those known to the art at that time. Such catalysts have been widely employed commercially. The alkali metal components are provided to the support by a variety of ways. The alkali metal can be supplied to the support as a salt and many salts of the alkali metals are described. Specific illustration is made of the use of alkali metal sulfates as one of many usable alkali metal compounds.

European Patent Application 85,237 describes an ethylene oxide catalyst wherein the applicants believe they "chemically absorbed" by alcohol wash, cesium and/or rubidium onto the catalyst support, a procedure not unlike that described by Neilsen and Schroer, supra, for potassium treated catalysts.

Japanese patent application Kokai 56/105,750 discloses, among other things, ethylene oxide catalysts containing cesium molybdate or cesium tungstate or cesium borate. The catalyst is stated to have an alumina carrier having a sodium content of less than 0.07 weight % and mainly consisting of alpha alumina having a specific surface area of 1 to 5 sg. m./gm. The carrier is impregnated with decomposible silver salt solution containing alkali metal boron complex, alkali metal molybdenum complex and/or alkali metal tungsten complex. No examples of mixtures of anions are disclosed, nor is there any disclosure or suggestion of mixtures of cesium with other alkali metals or alkaline earth metals. Japanese patent application Kokai 57/21937 discloses thallium containing catalysts in which the thallium may be a borate or titanate salt.

Since the date of filing of the Ser. No. 640,269 patent application, a number of patent documents have been published relating to ethylene epoxidation catalysts which may contain oxyanions. European patent application 247,414, published Dec. 12, 1987, discloses catalysts containing alkali metal and/or barium which may be provided as salts. The salts include nitrates, sulfates, and halides. European patent applications 266,015, published May 4, 1988, and 266,852, published May 11, 1988, disclose catalysts containing a rhenium component, e.g., rhenium oxide, rhenium cation or rhenate or perrhenate anion. An example of a catalyst made from silver oxalate with cesium hydroxide, ammonium perrhenate, and ammonium sulfate is disclosed in the '852 application. Numerous examples of silver catalysts containing cesium, rhenate and co promoter salts are presented in the '015 application. For instance, Experiment 7-12 reports a catalyst having 13.5 weight percent silver, 338 ppmw (parts per million by weight) cesium (CsOH), 186 ppmw rhenium ($NH_4ReO_4$) and 55 ppmw manganese ($KMnO_4$); Experiment 7-6, 12.7 wt%, 421 ppm cesium, 186 ppmw rhenium, 32 ppm sulfur (($NH_4)_2SO_4$) and Experiment 7-26, 14 7 wt% silver, 357 ppmw cesium and 78 ppmw potassium (as sulfate), 186 ppmw rhenium, 32 ppmw sulfur (($NH_4)_2SO_4$), and 184 ppmw tungsten ($H_2WO_4$). Experiments are presented in which vanadate, chlorate, molybdate, chromate, sulfite, phosphate and tungstate anion are added in combination with rhenate anion.

DISCLOSURE OF THE INVENTION

An aspect of this invention involves the manufacture of impregnated silver catalysts on a support, preferably an alpha-alumina support (having a size and configuration usable in commercially-operated ethylene oxide tubular reactors) having an alpha-alumina content (inclusive of binder) of at least 98 percent (98%) by weight, in which there is provided a mixture of at least one cesium salt and one or more alkali metal and alkaline earth metal salts.

The anions of cesium salts comprise oxyanions, preferably polyvalent oxyanions, of elements other than the oxygen therein having an atomic number of at least 15 to 83 and being from groups $3b$ through $7b$, inclusive, of the Periodic Table of the Elements (as published by The Chemical Rubber Company, Cleveland, Ohio, in *CRC Handbook of Chemistry and Physics*, 46th Edition, inside back cover). The salts of the alkali metals and/or alkaline earth metals present comprise at least one of halide of atomic numbers of 9 to 53, inclusive, and oxyanions of elements other than oxygen therein having an atomic number of either (i) 7 or (ii) 15 to 83, inclusive, and selected from the groups $3a$ to $7a$, inclusive, and $3b$ to $7b$, inclusive, of the Periodic Table of the Elements. Often the catalyst contains at least one anion other than an oxyanion of an element of groups $3b$ to $7b$.

It is understood that in the preparation of the catalysts, regardless of the specific salts of cesium and the one or more other alkali metal and/or alkaline earth metal, intermixing will occur. Hence, a catalyst prepared using cesium sulfate and potassium molybdate will also contain cesium molybdate and potassium sulfate.

The mixture is preferably in an amount sufficient relative to the amount of silver employed, to yield at STANDARD ETHYLENE OXIDE PROCESS CONDITIONS under oxygen process conditions, as hereinafter defined, a selectivity (or efficiency) of at least 79 percent. An aspect of the invention also involves the process of making ethylene oxide by feeding a gas phase mixture of ethylene, oxygen, recycled $CO_2$ and a gas phase inhibitor to a bed of impregnated silver catalyst of this invention, to produce ethylene oxide. The process for making ethylene oxide is not limited to STANDARD ETHYLENE OXIDE PROCESS CONDITIONS for definition as is the catalyst. Catalysts which have been subjected to process conditions for ethylene oxide manufacture such as STANDARD ETHYLENE OXIDE PROCESS CONDITIONS are considered an important aspect of this invention.

A remarkable aspect of a number of the various embodiments of this invention is the unique insensitivity of these catalysts to gas phase inhibitor addition. The catalysts of this aspect of the invention are active yet do not require critical doses of gas phase inhibitor for process control. Indeed, these catalysts tend to give a rather flat response to gas phase inhibitor addition making their use at commercial practice conditions efficient and free of upsets. Moreover, many of the catalysts of this invention exhibit unique high temperature responses yielding high selectivities at high temperatures (e.g., about 270° C.) as are obtained at normal operating temperatures (e.g., about 230°–250° C.). Many of the catalysts of this invention contain a cesium content which according to the prior art would be expected to poison the catalyst's capability for making ethylene oxide. Many of the catalysts of this invention depend upon a synergistic combination of alkali metal (in the salt form as herein defined) as spelled out in the aforementioned United Kingdom Patent No. 2,043,481, but the amounts of alkali metals to one another to achieve the desired synergy is now, according to this invention, not nearly as critical.

The catalysts of many various embodiments of this invention can employ in their manufacture roasting conditions considerably different from those employed previously. For example, in making these catalysts, one may use lower temperatures for shorter periods of time to achieve a highly active catalyst at the onset of use in making ethylene oxide.

DETAILED DESCRIPTION OF THE INVENTION

The process for making the catalyst and the catalysts of the invention are characterized in their preferred embodiment by either cesium or a combination of (a) cesium and (b) at least one other alkali metal of lithium, sodium, potassium and rubidium and/or alkaline earth metal of magnesium, calcium, strontium and barium, so as to achieve a synergistic result, i.e., an efficiency greater than the greater value obtainable under common conditions from respective catalysts which are the same as said catalyst except that instead of containing both (a) and (b), one contains the respective amount of (a), and the other contains the respective amount of (b), or an improvement in aging characteristics or gas phase inhibitor response by reason of the presence of the amount of (b). Preferably, the catalyst contains other alkali metal.

According to the most preferred aspects of this invention, the alkali metals are provided in the catalyst as salts whose anions are oxyanions as described previously. Catalysts in accord with this most preferred aspect, in general, are comprised of silver, cesium salts together with at least one other alkali metal (excluding francium) salt deposited onto the surface of a porous support, the particular mixture of silver and alkali metals being correlated in the most preferred embodiment to produce a synergistic result as defined in U.K. Patent 2,043,481 commonly assigned.

The invention as hereinafter described defines the binary alkali metal salt combinations of cesium lithium, cesium-sodium, cesium potassium and cesium-rubidium which in combination with silver which when employed under STANDARD ETHYLENE OXIDE PROCESS CONDITIONS provide a synergistic result for a particular catalyst carrier and catalyst preparation. The catalysts of the invention are not, however, restricted to the above combinations of alkali metal salts and alkaline earth metal salts. Other alkali metal salts and/or salts of other cations may advantageously be added to any of the aforementioned synergistic combinations for the purpose of raising or lowering the catalyst operating temperature, improving the initial catalyst activity during the start up period and/or improving the aging characteristics of the catalyst over prolonged periods of operation. In some instances, the addition of a third or even a fourth alkali metal salt and/or alkaline earth metal salt and/or other salt to an otherwise synergistic binary combination will effect a further increase in catalyst efficiency thus contributing to the synergistic result.

The techniques and relationships from which are derived synergistic binary alkali metal combinations for use in practicing the invention are described in considerable detail in United Kingdom Patent 2,043,481, and such description is incorporated herein by reference, specifically that disclosure at page 5, line 51 through page 11, line 6, inclusive.

As with any catalyst for making ethylene oxide which provides optimum performance, there exists a correlation between
(i) the nature of the support;
(ii) the amount of silver on or in the support;
(iii) the impurities or contaminants provided with the silver and other components; and
(iv) the conditions under which the catalyst is used to produce ethylene oxide.

In the above, for the purposes of this invention, "impurities or contaminants" can include the alkali metal salts defined above.

However, in attempting to define any catalyst there must be a base value from which other factors are determined especially when the factors are variables, each dependent upon the base value for meaning. In the case of this invention, the base value can be the amount of silver or a combination of the amount of silver and the nature of the support. In most cases the latter combination will be the base value. Because at least two values will comprise the base value for catalyst performance, it is apparent that correlations between such combinations and other factors can be quite complex. There is no common thread of logic which integrates all of these combinations and/or factors To that extent, practice of the invention requires experimental efforts to achieve all or essentially all of the benefits of this invention. Without departing from this script, one skilled in the art can readily achieve the optimum performances of the catalysts of this invention. It should be recognized that such script is commonly followed by the artisan in making any commercially employable ethylene oxide catalyst. The elements of the script are dependent upon the technology employed in making the catalyst.

The concentration of silver in the finished catalyst may vary from about 2 to 40 or more, often, 2 to 20 or more, weight percent, a commercially preferred range being from about 6% to about 16% by weight of silver. Lower silver concentrations are preferred from a cost per unit catalyst standpoint. However, the optimum silver concentration for any particular catalyst will be dependent upon economic factors as well as performance characteristics, such as catalyst efficiency, rate of catalyst aging and reaction temperature.

The concentration of cesium salt and other alkali metal and alkaline earth metal salts in the finished catalyst is not narrowly critical and may vary over a wide range. The optimum cesium salt and other alkali metal and/or alkaline earth metal salt concentration for a particular catalyst will be dependent upon performance characteristics, such as, catalyst efficiency, rate of catalyst aging and reaction temperature. The concentration of cesium salt in the finished catalyst may vary from about 0.0005 to 1.0 weight percent, preferably from about 0.005 to 0.1 weight percent. The ratio of cesium salt to other alkali metal and alkaline earth metal salt(s) to achieve desired performance is not narrowly critical and may vary over a wide range. The ratio of cesium salt to other alkali metal and alkaline earth metal salt(s) may vary from about 0.0001:1 to 10,000:1, preferably from about 0.001:1 to 1,000:1. Preferably, cesium comprises at least about 1 to 95, e.g., about 5 to 90, and often about 10 to 80, mole percent of the total moles of alkali metal and alkaline earth metal in the finished catalyst.

Carrier Selection

The catalyst carrier employed in practicing the invention may be selected from conventional, porous, refractory materials which are essentially inert to ethylene, ethylene oxide and other reactants and products at reaction conditions. These materials are generally labelled as "macroporous" and consist of porous materials having surface areas less than 10 sg. m/g (square meters per gm of carrier) and often is less than 1 sg. m/g. The surface area is measured by the conventional B.E.T. method described by Brunauer, S., Emmet, P., and Teller E., in *J. Am. Chem. Soc.* Vol. 60, pp. 309–16, (1938). They are further characterized by pore volumes ranging from about 0.15–0.8 cc/g, preferably from about 0.2–0.6 cc/g. Pore volumes may be measured by conventional mercury porosimetry or water absorption techniques. Median pore diameters for the above described carriers range from about 0.01 to 100 microns. a more preferred range being from about 0.5 to 50 microns. The carriers may have monomodal, bimodal pore, or multimodal distributions.

For ease of repeatability in the use and reuse of impregnating solutions, the carrier should preferably not contain ions which are exchangeable with the alkali and alkaline earth metals supplied to the catalyst, either in the preparation or use of the catalyst, so as to upset the amount of alkali metal which provides the desired performance and/or catalyst enhancement. If the carrier contains such ions, the ions should generally be removed by standard chemical techniques such as leaching. However, if the carrier contains an amount of alkali metal or alkaline earth metal, which is transferable to the silver, then either (i) the carrier may be treated to remove such excess alkali metal or alkaline earth metal or (ii) the amount of alkali metal or alkaline earth metal supplied to the catalyst should take into account the transferred alkali metal or alkaline earth metal.

The chemical composition of the carrier, which may be an inert refractory oxide, is not narrowly critical. Carriers may be composed, for example, of alpha alumina, silicon carbide, silicon dioxide, zirconia, magnesia and various clays. The preferred carriers are alpha-alumina particles often bonded together by a bonding agent and have a very high purity, i.e., at least 98 wt. % alpha alumina, any remaining components being silica, alkali metal oxides (e.g., sodium oxide) and trace amounts of other metal and non-metal impurities; or they may be of lower purity, i.e., about 80 wt. % alpha-alumina, the balance being a mixture of silicon dioxide, various alkali oxides, alkaline earth oxides, iron oxides, and other metal and non metal oxides. The carriers are formulated so as to be inert under catalyst preparation and reaction conditions. A wide variety of such carriers are commercially available. Alumina carriers are manufactured by United Catalysts, Inc., Louisville, Kentucky, and the Norton Company, Akron, Ohio. As stated above, processes for making carriers is often kept a trade secret by the manufacturers. Various alpha-alumina carriers are disclosed, for instance, U.S. Pat. Nos. 3,172,866; 3,908,002; 4,136,063; 4,379,134; 4,368,144; 4,389,338; 4,645,754; and 4,701,437; European Patent Applications 207,550; 207,541; 244,895; 266,852; and 266,015; and the Peoples Republic of China Patent application CN 85 1-02281A.

The carriers may be in the shape of pellets, extruded particles, spheres, rings and the like. The size of the carriers may vary from about 1/16" to ½". The carrier size is chosen to be consistent with the type of reactor employed. In general, sizes in the range of ⅛" to ⅜" have been found to be most suitable in the typical fixed bed, tubular reactor used in commercial operations.

While as with any supported catalyst, the optimal performance will depend upon optimizing the carrier in terms of its chemical composition (including impurities), surface area, porosity and pore volume. However, the enhancement in performance provided by this invention may be most pronounced when using less than optimized carriers. Thus, in demonstrating the invention in the examples, a variety of carriers are used.

It has been stated in some patents that there exists a correlation between surface area of the support and the amount of alkali metal promoter one may employ to maximize the selectivity capabilities of the catalyst, see U.S. Pat. Nos. 3,962,136 and 4,207,210. This invention demonstrates that by the use of the alkali metal salts of this invention, such a relationship does not exist and amounts of alkali metal salts far greater (based on alkali content) than that previously urged desirable can be employed to produce the best performing catalysts as judged by present day commercial standards.

Oxyanions and Other Anions

The types of oxyanions suitable as counterions for the alkali and alkaline earth metals provided in the catalysts of this invention comprise by way of example only, sulfate, $SO_4^{-2}$, phosphates, e.g., $PO_4^{-3}$, manganates, e.g., $MnO_4^{-2}$, titanates, e.g., $TiO_3^{-2}$, tantalates, e.g., $Ta_2O_6^{-2}$, molybdates, e.g., $MoO_4^{-2}$, vanadates, e.g., $V_2O_4^{-2}$, chromates, e.g., $CrO_4^{-2}$, zirconates, e.g., $ZrO_3^{-2}$, polyphosphates, nitrates, chlorates, bromates, tungstates, thiosulfates, cerates, and the like. The halide ions include fluoride, chloride, bromide and iodide. It is well recognized that many anions have complex chemistries and may exist in one or more forms, e.g., manganate ($MnO_4^{-2}$) and permanganate ($MnO_4^{-1}$); orthovanadate and metavanadate; and the various molybdate oxyanions such as $MoO_4^{-2}$, $Mo_7O_{24}^{-6}$ and $Mo_2O_7^{-2}$. While an oxyanion, or a precursor to an oxyanion, may be used in solutions impregnating a carrier, it is possible that during the conditions of preparation of the catalyst and/or during use, the particular oxyanion or precursor initially present may be converted to another form which may be an anion in a salt or even an oxide such as a mixed oxide with other metals present in the catalyst. In many instances, analytical techniques may not be sufficient to precisely identify the species present. The invention is not intended to be limited by the exact species that may ultimately exist on the catalyst during use but rather reference herein to oxyanions is intended to provide guidance to understanding and practicing the invention.

Frequently, in the finished catalyst the calculated ratio of A/n:Cs, wherein A is the moles of oxyanion of elements of group 3b to 7b and n is the valence of such oxyanion and Cs is the moles of cesium, is at least about 1:10, preferably at least about 3:10. When a nitrate anion is employed, generally the catalyst contains sodium or, preferably, potassium, and the nitrate comprises at least 20, say, at least 50, mole percent of the total anion associated with alkali metals and alkaline earth metals. In some instances, it has been found beneficial to add more anion than is required to associate with the alkali metal and alkaline earth metal being provided to the catalyst. The reason why such additional anion is beneficial in these situations is not known. The additional anion may be added in the form of an acid, an ammonium salt, an amine salt, etc., or a portion of the alkali metal and/or alkaline earth metal may be added as an acid salt, e.g., potassium hydrogen sulfate.

Catalyst Preparation

A variety of procedures may be employed for preparing catalysts containing the aforementioned cesium salts, alone or with one or more other alkali metal salts (excluding francium salts), and/or alkaline earth metal salts or other salts in accordance with the present invention. The preferred procedure comprises: (1) impregnating a porous catalyst carrier with a solution comprising a solvent or solubilizing agent, silver complex in an amount sufficient to deposit the desired weight of silver upon the carrier, and the aforementioned alkali metal and alkaline earth metal salts sufficient to deposit respective amounts of them on the support such that the efficiency of ethylene oxide manufacture of the finished catalyst when tested at STANDARD ETHYLENE OXIDE PROCESS CONDITIONS under oxygen process conditions is at least 79 percent and (2) thereafter treating the impregnated support to convert the silver salt to silver metal and effect deposition of silver, and the alkali metal and alkaline earth metal salts on the exterior and interior surfaces of the support. Silver and alkali (and alkaline earth) metal salt deposition are generally accomplished by heating the carrier at elevated temperatures to evaporate the liquid within the support and effect deposition of the silver and metal salt onto the interior and exterior carrier surfaces. Impregnation of the carrier is the preferred technique for silver deposition because it utilizes silver more efficiently than coating procedures, the latter being generally unable to effect substantial silver deposition onto the interior surfaces of the carrier. In addition, coated catalysts are more susceptible to silver loss by mechanical abrasion.

The sequence of impregnating or depositing the surfaces of the carrier with silver and alkali and alkaline earth metal salts is optional. Thus, impregnation and deposition of silver and alkali and/or alkaline earth metal salts may be effected coincidentally or sequentially, i.e., the alkali and/or alkaline earth metal salts may be deposited prior to, during, or subsequent to silver addition to the carrier. The alkali metal salts may be deposited together or sequentially. For example, cesium salts may be deposited first, followed by the coincidental or sequential deposition of silver and the other alkali or alkaline earth metal salts, or such other alkali or alkaline earth metal salts may be deposited first followed by coincidental or sequential deposition of silver and cesium salt.

Impregnation of the catalyst carrier is effected using one or more solutions containing silver and alkali metal and/or alkaline earth metal salts in accordance with well known procedures for coincidental or sequential depositions. For coincidental deposition, following impregnation the impregnated carrier is heat or chemically treated to reduce the silver compound to silver metal and deposit the metal salts onto the catalyst surfaces.

For sequential deposition, the carrier is initially impregnated with silver or alkali and/or alkaline earth metal salt (depending upon the sequence employed) and then heat or chemically treated as described above. This is followed by a second impregnation step and a corresponding heat or chemical treatment to produce the finished catalyst containing silver and salts.

In making the catalysts of this invention, the alkali and alkaline earth metal salts have such high melting temperatures that when deposited on the support with silver compound, and subject to heating to convert the silver compound to silver metal, the salts preferably remain essentially unchanged. Of course, it is realized that alkali metal and alkaline earth metal salts having an unstable oxidation state will change to a stable oxidation state or states, e.g., sulfites to sulfates. Alkali metal and alkaline earth metal salts used in this invention having a stable oxidation state will remain essentially unchanged. This is contrary to what occurs when, e.g., alkali metal is deposited as the hydroxide or carbonate both of which may transform to different salt form (e.g. nitrate) during the heating (roasting) step depending on the roast conditions, see Nielsen and Schroer, supra, and/or during use.

The silver solution used to impregnate the carrier is comprised of a silver compound in a solvent or complexing/solubilizing agent such as the silver solutions disclosed in the art. The particular silver compound employed may be chosen, for example, from among silver complexes, nitrate, silver oxide or silver carboxylates, such as, silver acetate, oxalate, citrate, phthalate, lactate, propionate, butyrate and higher fatty acid salts. Desirably, silver oxide complexed with amines is the preferred form of silver in the practice of the invention.

A wide variety of solvents or complexing/solubilizing agents may be employed to solubilize silver to the desired concentration in the impregnating medium. Among those disclosed in the art as being suitable for this purpose are lactic acid (U.S. Pat. Nos. 2,477,436 to Aries; and 3,501,417 to DeMaio); ammonia (U.S. Pat. No. 2,463,228 to West, et al); alcohols, such as ethylene glycol (U.S. Pat. Nos. 2,825,701 to Endler, et al.,; and 3,563,914 to Wattimina); and amines and aqueous mixtures of amines (U.S. Pat. Nos. 2,459,896 to Schwarz; 3,563,914 to Wattimina; 3,215,750 to Benisi; 3,702,259 to Nielsen; and 4,097,414, 4,374,260 and 4,321,206 to Cavitt).

Following impregnation of the catalyst carrier with silver and alkali metal and/or alkaline earth metal salts, the impregnated carrier particles are separated from any remaining non absorbed solution. This is conveniently accomplished by draining the excess impregnating medium or, alternatively, by using separation techniques, such as filtration or centrifugation. The impregnated carrier is then generally heat treated (e.g., roasted) to effect decomposition and reduction of the silver metal compound (complexes in most cases) to metallic silver and the deposition of alkali metal and alkaline earth metal salt. Such roasting may be carried out at a temperature of from about 100° C. to 900° C., preferably from 200° to 700° C., for a period of time sufficient to convert substantially all of the silver salt to silver metal. In general, the higher the temperature, the shorter the required reduction period. For example, at a temperature of from about 400° C. to 900° C., reduction may be accomplished in about 1 to 5 minutes. Although a wide range of heating periods have been suggested in the art to thermally treat the impregnated support (e.g., U.S. Pat. No. 3,563,914 suggests heating for less than 300 seconds to dry, but not roast to reduce, the catalyst, U.S. Pat. No. 3,702,259 discloses heating from 2 to 8 hours at a temperature of from 100° C. to 375° C. to reduce the silver salt in the catalyst; and U.S. Pat. No. 3,962,136 suggests ½ to 8 hours for the same temperature range), it is only important that the reduction time be correlated with temperature such that substantially complete reduction of the silver salt to metal is accomplished. A continuous or step-wise heating program is desirably used for this purpose. Continuous roasting of the catalyst for a short period of time, such as for not longer than ½ hour is preferred and can be effectively done in making the catalysts of this invention. A special attribute of the catalysts of this invention is that they are more amenable to roasting at lower temperatures, such as lower than about 500° C., than the catalysts of U.K. Patent 2,043,481, without the sacrifice of performance characteristics.

Heat treatment is preferably carried out in air, but a nitrogen or carbon dioxide atmosphere may also be employed. The equipment used for such heat treatment may use a static or flowing atmosphere of such gases to effect reduction, but a flowing atmosphere is much preferred.

An important consideration in making the catalyst of this invention is to avoid the use of strongly acidic or basic solutions which can attack the support and deposit impurities which can adversely affect the performance of the catalyst. Acidic or basic components which do not adversely affect the catalyst can be, and are often, used, e.g., amines and compounds to provide the desired anions such as sulfuric acid, ammonium sulfate, molybdic acid, and the like. These compounds may be present in greater than the amounts required for stoichiometric combination. The preferred impregnation procedure of U.K. Patent 2,043,481 coupled with the high roasting temperature, short residence time procedure which the patent also described is especially beneficial in minimizing such catalyst contamination. However, the use of the salts of this invention coupled with the high purity supports allows one to use lower temperatures though short residence times ar preferred.

The particle size of silver metal deposited upon the carrier is asserted by a portion of the prior art to be a function of the catalyst preparation procedure employed. This may seem to be the case because of the limited ability of the art to effectively view the surface of the catalyst. Thus the space between the silver particles seen on the carrier has not been characterized sufficiently to say whether only such particles of silver represent the silver on the carrier. However, the particular choice of solvent and/or complexing agent, silver compound, heat treatment conditions and catalyst carrier may affect, to varying degrees, the range of the size of the resulting silver particles seen on the carrier. For carriers of general interest for the production of ethylene oxide, a distribution of silver particles sizes in the range of 0.005 to 2.0 microns is typically obtained. However, the role of particle size of the silver catalyst upon the effectiveness of the catalyst in making ethylene oxide is not clearly understood. In view of the fact that the silver particles are known to migrate on the surface of the catalyst when used in the catalytic reaction resulting in a marked change in their size and shape while the catalyst is still highly effective suggests that the silver particle size viewed on the support surfaces of the catalyst may not be a significant factor in catalytic performance

Ethylene Oxide Production

The silver catalysts of the invention are particularly suitable for use in the production of ethylene oxide by the vapor phase oxidation of ethylene with molecular oxygen. The reaction conditions for carrying out the oxidation reaction are well-known and extensively described in the prior art. This applies to reaction conditions, such as temperature, pressure, residence time, concentration of reactants, gas phase diluents (e.g., nitrogen, methane and $CO_2$), gas phase inhibitors (e.g., ethylene dichloride), and the like. The gases passed to the reactor may contain modifiers or inhibitors or additives such as disclosed by Law, et al., in U.S. Pat. Nos. 2,279,469 and 2,279,470, such as nitrogen oxides and nitrogen oxides generating compounds. See also, European Patent No. 3642. In addition, the desirability of recycling unreacted feed, or employing a single-pass system, or using successive reactions to increase ethylene conversion by employing reactors in series arrangement can be readily determined by those skilled in the art. The particular mode of operation selected will usually be dictated by process economics.

Generally, the commercially practiced processes are carried out by continuously introducing a feed stream containing ethylene and oxygen to a catalyst-containing reactor at a temperature of from about 200° C. to 300° C., and a pressure which may vary from about five atmospheres to about 30 atmospheres depending upon the mass velocity and productivity desired. Residence times in large scale reactors are generally on the order of about 0.1 5 seconds. Oxygen may be supplied to the reaction in an oxygen-containing stream, such as air or as commercial oxygen. The resulting ethylene oxide is separated and recovered from the reaction products using conventional methods. However, for this invention, the ethylene oxide process envisions the normal gas recycle encompassing carbon dioxide recycle in the normal concentrations.

STANDARD ETHYLENE OXIDE PROCESS CONDITIONS

The STANDARD ETHYLENE OXIDE PROCESS CONDITIONS (ABBR. "CONDITIONS") for characterizing the catalysts of this invention involves the use of a standard backmixed autoclave with full gas recycle including carbon dioxide. The CONDITIONS may be operated with some variation in ethylene, oxygen and gas phase inhibitor feed. Two cases are illustrated: air process conditions, which simulates in the backmixed reactor the typical conditions employed in commercial air type ethylene oxide processes where air is used to supply the molecular oxygen and the oxygen process conditions, which simulates in the backmixed reactor the typical conditions in commercial oxygen type ethylene oxide processes where molecular oxygen, as such, is employed. Each case provides a different efficiency but it is the rule for practically all cases that air as the oxygen feed, using lower amounts of oxygen and ethylene, will yield an efficiency to ethylene oxide which is about 2 to 4 percentage points lower than that when molecular oxygen is employed as oxygen feed. The CONDITIONS employ the well known backmixed bottom agitated "Magnedrive" autoclaves described in FIG. 2 of the paper by J. M. Berty entitled "Reactor for Vapor Phase Catalytic Studies", in *Chemical Engineering Progress*, Vol. 70 No. 5, pages 78–84. 1974. The CONDITIONS employ 1.0 mole % ethylene oxide in the outlet gas of the reactor under the following standard inlet conditions:

| Component | Air process Conditions, Mole % | Oxyen process Conditions, Mole % |
|---|---|---|
| Oxygen | 6.0 | 8.0 |
| Ethylene | 8.0 | 30 |
| Ethane | 0.5 | 0.5 |
| Carbon Dioxide | 6.5 | 6.5 |
| Nitrogen | Balance of Gas | Balance of Gas |
| Parts per million ethyl chloride (or one-half such amount when ethylene dichloride is used) | 7.5 | 10 |

The pressure is maintained constant at 275 psig and the total outlet flow is maintained at 22.6 SCFH. SCFH refers to cubic feet per hour at standard temperature and pressure, namely, 0° C. and one atmosphere. The outlet ethylene oxide concentration is maintained at 1.0% by adjusting the reaction temperature. Thus, temperature (° C.) and catalyst efficiency are obtained as the responses describing the catalyst performance.

The catalyst test procedure used in the CONDITIONS involves the following steps:

1. 80 cc of catalyst is charged to the backmixed autoclave. The volume of catalyst is measured in 1" I.D. graduated cylinder after tapping the cylinder several times to thoroughly pack the catalyst. The volume of catalyst is alternatively calculated from the packing density of the carrier and the amount of silver and additives. The weight of the catalyst is noted.

2. The backmixed autoclave is heated to about reaction temperature in a nitrogen flow of 20 SCFH with the fan operating at 1500 rpm. The nitrogen flow is then discontinued and the above described feed stream is introduced into the reactor. The total gas outlet flow is adjusted to 22.6 SCFH. The temperature is adjusted over the next few hours so that the ethylene oxide concentration in the outlet gas is approximately 1.0%.

3. The outlet oxide concentration is monitored over the next 4-6 days to make certain that the catalyst has reached its peak steady state performance. The temperature is periodically adjusted to achieve 1% outlet oxide. The selectivity of the catalyst to ethylene oxide and the temperature are thus obtained.

The standard deviation of a single test result reporting catalyst efficiency in accordance with the procedure described above is 0.7% efficiency units. The running of a multiplicity of tests will reduce the standard deviation by the square root of the number of tests.

The specific STANDARD ETHYLENE OXIDE PROCESS CONDITIONS are used in the examples below unless indicated otherwise. In commercial processes, typical operating conditions can vary and the amounts of the ingredients employed can be adjusted to achieve the best efficiencies. In particular the amounts of ethane, carbon dioxide and organic chloride can be varied to optimize efficiency for the manufacture of ethylene oxide. Ethane is an impurity contained in varying amounts in ethylene raw material. Ethane can also be added to a commercial reactor to provide better control of the chloride's inhibitor action. Typically, the amount of ethane used in commercial processes can vary from about 0.001 to about 5 mole percent for achieving optimization under both air process conditions and oxygen process conditions. As the concentration of ethane increases in the reactor, the effective surface chloride concentration on the catalyst is believed to be decreased, thereby decreasing the ability of chloride to promote/inhibit reactions that increase efficiency for the manufacture of ethylene oxide. The amount of chloride, e.g., ethyl chloride or ethylene dichloride, can be varied to provide the needed promoter/inhibitor action commensurate with the ethane levels encountered in a particular process and the type of alkali and alkaline earth metal salt used in the catalyst. The amount of organic chloride used in commercial processes can typically vary from about 1.0 ppm to about 100 ppm for achieving optimization under both air process conditions and oxygen process conditions. Carbon dioxide is generally considered an inhibitor, and the inhibitor effect of carbon dioxide on process efficiency may be variable with its concentration. With different types of alkali metal and alkaline earth metal salts used in preparation of the catalysts of this invention, different concentrations of carbon dioxide may be more desirable in certain commercial processes. Typically, the amount of carbon dioxide used in commercial processes can vary from about 2 to about 15 mole percent for achieving optimization under both air process conditions and oxygen process conditions. The amount of carbon dioxide is dependent on the size and type of carbon dioxide scrubbing system employed. The optimization of the amounts of ethane, carbon dioxide and organic chloride provides catalysts which are especially suitable for obtaining desired efficiencies in commercial ethylene oxide manufacture. Catalysts which have been subjected to process conditions for ethylene oxide manufacture such as STANDARD ETHYLENE OXIDE PROCESS CONDITIONS are considered an important aspect of this invention.

The following detailed procedures are provided as illustrative of methods and carriers which are useful for preparing catalysts according to the invention. These examples are by way of illustration only and are not to be construed as limiting the scope of the invention described herein.

Typical alpha alumina carriers useful in practicing this invention are the following:

| CARRIER "A" | |
|---|---|
| Chemical Composition of Carrier "A" | |
| alpha-Alumina | 98.57 wt. % |
| Impurities (in bulk): | |
| $SiO_2$ | .99 wt. % |
| CaO | .008 wt. % |
| $Na_2O$ | .226 wt. % |
| $Fe_2O_3$ | .034 wt. % |
| $K_2O$ | |
| Physical Properties of Carrier "A" | |
| Surface Area (1) | 0.36-0.55 m²/g typically between 0.40 and 0.50 m²/g |
| Pore Volume (2) (or water absorption) | 0.52 cc/g |
| Packing Density (3) | 0.71 g/ml |
| Median Pore diameter (4) | 20-30 microns |
| Pore size Distribution, % Total Pore Volume (4) | |
| Pore Size Microns | % Total Pore Volume |
| <0.1 | 0.0 |
| 0.1-1.0 | About 6.0 |
| 1.0-10.0 | 37.0 |
| 10.0-30.0 | 16.0 |
| 30.0-100 | 32.0 |
| >100 | 9.0 |

| CARRIER "B" | |
|---|---|
| Chemical Composition of Carrier "B" | |
| alpha-Alumina | about 99.5 + wt. % |
| Acid Leachable Impurities: | |
| Leachate contained 5 ppm $SO_4^{-2}$, 18 ppm $Na^+$, 1.4 ppm $Li+$, 1 ppm $Cl^-$, 2 ppm $NO_3^-$ | |
| Physical Properties of Carrier "B" | |
| Surface Area (1) | 0.43 m²/g |
| Pore Volume (2) | 0.44 cc/g |
| Packing Density (3) | 0.705 g/cc |
| Median Pore Diameter (4) | 10.2 microns |
| Pore size Distribution, % Total Pore Volume (4) | |
| Pore Size, Microns | % Total Pore Volume |
| <0.1 | 0 |
| 0.1-1.0 | 0 |
| 1-10 | 51.4 |
| 10-30 | 4.6 |
| 30-100 | 21.0 |
| >100 | 23.0 |

| CARRIER "C" | |
|---|---|
| Chemical Composition of Carrier "C" | |
| alpha-Alumina | about 99.84 wt. % |
| Impurities (in bulk) | |
| $Na_2O$ | 0.02 wt. % |
| $K_2O$ | 0.01 wt. % |
| $SiO_2$ | 0.01 wt. % |
| Oxides of Ca and Mg | 0.03 wt. % |
| Acid Leachable Impurities: | |
| Leachate contained 80 ppm $Na^+$, 17 ppm $K^+$. | |
| Physical Properties of Carrier "C" | |
| Surface Area (1) | 0.436 m²/g |
| Pore Volume (2) | 0.502 cc/g |
| Packing Density (3) | 0.696 g/cc |
| Median Pore Diameter (4) | 20.0 microns |
| Apparent Porosity (%) | 66.3 |
| % Water Absorption | 50.0 |
| Attrition Loss/Hr. (%) | 23.2 |
| 25 Ft. Drop Test (% Passing) | 97 |
| Crush Strength Averae, lbs. | 14.9 |
| Pore Size Distribution, % Total Pore Volume (4) | |
| | Total |

-continued

| Pore Size, Microns | Pore Volume |
|---|---|
| $P_1$ (<0.1) | 0 |
| $P_2$ (0.1–0.5) | 2.0 |
| $P_3$ (0.5–1.0) | 5.5 |
| $P_4$ (1.0–10.0) | 35.0 |
| $P_5$ (10.0–100) | 53.0 |
| $P_6$ (>100) | 4.5 |

CARRIER "D"

Chemical Composition of Carrier "D"

| | |
|---|---|
| alpha-Alumina | about 99.5 + wt. % |
| Acid Leachable Impurities: | |
| Leachate contained 4 pm $Na^+$, less than | |
| 0.01 ppm $K^+$, less than 0.01 ppm $Ca^{++}$, less than | |
| 0.01 ppm $Mg^{++}$. | |

Physical Properties of Carrier "D"

| | |
|---|---|
| Surface Area (1) | 0.487 $m^2$/g |
| Pore Volume (2) | 0.429 cc/g |
| Packing Density (3) | 41.64 lbs/$ft^3$ |
| Median Pore Diameter (4) | 47 microns |
| Apparent Porosity (%) | 65 |
| % Water Absorption | 48.9 |
| Crush Strength Average, lbs. | 9.0 |

Pore Size Distribution, % Total Pore Volume (4)

| Pore Size, Microns | % Total Pore Volume |
|---|---|
| $P_1$ (<0.1) | 0 |
| $P_2$ (0.1–0.5) | 2.0 |
| $P_3$ (0.5–1.0) | 7.0 |
| $P_4$ (1.0–10.0) | 30.0 |
| $P_5$ (10.0–100) | 26.0 |
| $P_6$ (>100) | 35.0 |

CARRIER "E"

Carrier E is an alpha-alumina carrier prepared by calcining to a maximum temperature of about 1025° C., gamma-alumina (available as N-6573 from the Norton Company, Akron, Oh.) in the presence of about 3.55 weight percent aluminum fluoride as fluxing agent. The carrier contains at least 99.0 weight percent alpha alumina, about 0.2 weight percent fluoride and as water leachable components:

| | |
|---|---|
| aluminum | 132 ppmw |
| calcium | 50 ppmw |
| magnesium | 5 ppmw |
| sodium | 66 ppmw |
| potassium | 14 ppmw |
| fluoride | 425 ppmw |
| nitrate | 1 ppmw |
| phosphate | 11 ppmw |
| fluorophosphate | 2 ppmw |
| sulfate | 6 ppmw |
| silicon | 10 ppmw |

Physical Properties of Carrier "E"

| | |
|---|---|
| Surface Area (1) | 1.17 $m^2$/g |
| Pore Volume (2) | 0.68 cc/g |
| Median Pore Diameter (3) | 1.8 microns |
| Packing Density (4) | 0.53 g/ml. |

Pore Size Distribution, % Total Pore Volume (4)

| Pore Size, Microns | % Total Pore Volume |
|---|---|
| $P_1$ (<0.1) | 0 |
| $P_2$ (0.1–0.5) | 2.0 |
| $P_3$ (0.5–1.0) | 9.5 |
| $P_4$ (1.0–10.0) | 84.5 |
| $P_5$ (10.0–100) | 1.0 |
| $P_6$ (>100) | 3.0 |

CARRIER "F"

Carrier F is an alpha-alumina carrier prepared by calcining to a maximum temperature of about 1100° C., gamma alumina (N-6573) which had been impregnated with an aqueous 1M ammonia fluoride solution. The carrier contains at least 99.0 weight percent alpha-alumina and about 0.2 weight percent fluoride and has a surface area of 1.1 square meters per gram, a pore volume of 0.76 cubic centimeters per gram and a packing density of about 0.52 grams per milliliter.

CARRIER "G"

Carrier G is an alpha-alumina carrier prepared by calcining to a maximum temperature of about 1100° C., gamma alumina (N 6573) which had been impregnated with aqueous 1M ammonium fluoride solution. The carrier contains at least 99.0 weight percent alpha alumina and about 0.25 weight percent fluoride and has a surface area of 1.0 square meter per gram, a pore volume of 0.76 cubic centimeters per gram and a packing density of 0.52 grams per milliliter.

CARRIER "H"

Carrier H is an alpha-alumina carrier prepared by calcining to a maximum temperature of about 1100° C., gamma-alumina (available as N 7759 from The Norton Company) which has been impregnated with aqueous 1M ammonia fluoride solution. The carrier contains at least 99.0 weight percent alpha-alumina and about 0.62 weight percent fluoride and has a surface area of 1.0 square meter per gram, a pore volume of 0.74 cubic centimeters per gram and a packing density of 0.49 grams per milliliter.

CARRIER "I"

Carrier I is a high purity (99.3), alpha-alumina support containing as acid leachable components (Inductively Coupled Plasma Spectroscopy):

| Element | PPM (Weight) |
|---|---|
| Ag | 0.2 |
| Al | 164 |
| B | 0.2 |
| Ba | 0.3 |
| Ca | 83 |
| Cd | less than 0.1 |
| Co | less than 0.1 |
| Cr | less than 0.1 |
| Cu | less than 0.1 |
| Fe | 2 |
| Mg | 6 |
| Na | 130 |
| Pb | 0.5 |
| Sb | 0.7 |
| Si | 104 |
| Sn | 0.7 |
| Ti | 7 |
| V | 7 |
| Zn | 0.2 |

The carrier has an average pore diameter of 0.54 micron, a pore volume of about 0.31 cc/g, and a surface area of about 0.8 square meter per gram.

(1) Method of Measurement described in "Adsorption Surface Area and Porosity", S. J. Gregg and K. S. W. Sing, Academic Press (1967), pages 316–321.
(2) Method of Measurement as described in ASTM C20-46.
(3) Calculated value based on conventional measurement of the weight of the carrier in a known volume container.
(4) Method of Measurement described in "Application of Mercury Penetration to Materials Analysis", C. Orr, Jr., Powder Technology, Vol. 3, pp. 117–123 (1970).

Attrition Loss and Crush Strength Average and Range were determined according to Test No. 45 and Test No. 6, respectively, as referred to in Catalyst Carriers Norton Company, Akron, Ohio Bulletin CC-11, 1974. 25 Ft. Drop Test was determined by dropping carrier pills through a tube for a vertical distance of 25 feet onto a steel plate and observing for breakage. Non-breakage of carrier pills indicated percent passing. Acid Leachable Impurities were determined by contacting carrier pills with 10% nitric acid for one hour and determining extracted cations by standard Atomic Absorption spectroscopy techniques. Inductively Coupled Plasma Spectroscopy techniques may also be used for such determinations.

Catalyst Preparation Techniques

The carrier, as indicated, was impregnated under vacuum as hereinafter described with a solution of silver complex and alkali metal and alkaline earth metal salts. The alkali metal and/or alkaline earth metal containing components need not be introduced as the salts. For instance, cesium hydroxide may be used in conjunction with an ammonium salt (e.g., ammonium sulfate) or acid (e.g., sulfuric acid) or organic compound (e.g., ethylsulfonate) and under conditions of catalyst preparation or use, conversion is made to the desired species. The impregnating solution was prepared at a concentration such that the finished catalyst contained the desired amounts of silver cesium salt and/or the other alkali metal and/or alkaline earth metal salts. The required concentration of silver and alkali metal and alkaline earth metal salts in solution for the given carrier is calculated from the packing density (grams/cc) and pore volume of the carrier which are either known or readily determined. Assuming that all of the silver in the impregnating solution contained in the pores of the carrier is deposited upon the carrier, approximately 21 wt. % silver in solution is necessary to prepare a catalyst containing about 11 wt. % silver on the catalyst. This relationship can vary depending upon the nature of the carrier, e.g., pore volume of the carrier may influence the amount of silver deposited from a given solution. The required concentration of alkali metal or alkaline earth metal salts in solution is obtained by dividing the solution silver concentration by the ratio of silver to alkali metal or alkaline earth metal salts desired in the finished catalyst. Thus, to obtain 11.0 wt. % Ag and 0.0047 wt. % Cs, the ratio is approximately 2330 and the required cesium concentration in solution is 0.009 wt. %. The solution containing the desired concentrations of silver and alkali metal and alkaline earth metal salts was prepared as described below.

Impregnating Solution Preparation

The indicated amounts of ethylenediamine (high purity grade) were mixed with indicated amounts of distilled water. Then oxalic acid dihydrate (reagent grade) was then added slowly to the solution at ambient temperature (23° C) while continuously stirring. During this addition of oxalic acid, the solution temperature rose to about 40° C. due to the reaction exotherm. Silver oxide powder (Metz Corporation) was then added to the diamine oxalic acid salt-water solution while maintaining the solution temperature below about 40° C. Finally, monoethanolamine, aqueous alkali metal salt solution(s) and distilled water were added to complete the solution. The specific gravity of the resulting solution was about 1.3–1.4 g/ml.

Catalyst Preparation

Carrier was impregnated in a 12 inches long ×2 inches I.D. glass cylindrical vessel equipped with a suitable stopcock for draining the carrier after impregnation. A suitable size separatory funnel for containing the impregnating solution was inserted through a rubber stopper equipped with a metal tube for attaching a vacuum line into the top of the impregnating vessel. The impregnating vessel containing the carrier was evacuated to approximately 2 inches of mercury pressure for about 20 minutes after which the impregnating solution was slowly added to the carrier by opening the stopcock between the separatory funnel and the impregnating vessel until the carrier was completely immersed in solution, the pressure within the vessel being maintained at approximately 2 inches of mercury. Following addition of the solution, the vessel was opened to the atmosphere to attain atmospheric pressure, the carrier then remained immersed in the impregnating solution at ambient conditions for about 1 hour, and thereafter drained of excess solution for about 30 minutes. The impregnated carrier was then heat treated as follows (unless stated otherwise) to effect reduction of silver salt and deposition of alkali metal salts on the surface. The impregnated carrier was spread out in a single layer on a 2⅜ inches wide endless stainless steel belt (spiral weave) and transported through a 2 inches ×2 inches square heating zone for 2.5 minutes, the heating zone being maintained at 500° C by passing hot air upward through the belt and about the catalyst particles at the rate of 266 SCFH. The hot air was generated by passing it through a 5 ft. long ×2 inches I.D. stainless steel pipe which was externally heated by an electric furnace (Lindberg TM tubular furnace: 2½ inches I.D., 3 feet long heating zone) capable of delivering 5400 watts. The heated air in the pipe was discharged from a square 2 inches ×2 inches discharge port located immediately beneath the moving belt carrying the catalyst carrier. After being roasted in the heating zone, the finished catalyst was weighed, and, based upon the weight gain of the carrier and the known ratios of silver to alkali metal salt in the impregnating solution, it was calculated to contain the wt. % of silver, and wt. % alkali metal salts indicated.

The analysis for silver was carried out by the following method: An approximately 50 g sample of catalyst was powdered in a mill and 10 g of the powdered sample weighed to the nearest 0.1 mg. The silver in the catalyst sample was dissolved in hot (80° C.) 50%, by volume, nitric acid solution. The insoluble alumina particles were filtered and washed with distilled water to remove all adhering nitrate salts of Ag, Cs, etc. This solution was made up to 250 ml in a volumetric flask using distilled water. A 25 ml aliquot of this solution was titrated according to standard procedures using a 0.1 Normal solution of ammonium thiocyanate and ferric nitrate as indicator. The amount of Ag so determined in 250 ml solution was then used to calculate the weight percent silver in the catalyst sample.

Silver and alkali metal concentrations for all catalysts described in the specification are calculated values as described above.

Carriers are nominally ring shape having dimensions of about ⅛×5/16 x 5/16 inch or about ⅛×¼×¼ inch.

EXAMPLE 1

| Ingredients | |
|---|---|
| Carrier "A" | 150 g |
| Ethylenediamine (High Purity Grade) | 49.62 gms |
| Distilled Water | as indicated |
| Oxalic Acid Dihydrate (Reagent Grade) | 49.70 gms |
| Silver Oxide Powder (Metz) | 87.10 gms |
| Monoethanolamine, Fe + Cl free | 17.41 gms |

-continued

| Ingredients | |
|---|---|
| Aqueous Cs Solution as sulfate (.01453 g Cs/g solution or 0.1180 g Cs) | 8.12 gms |
| Aqueous K Solution as sulfate (.01580 g K/g solution or 0.2948 g K) | 18.66 gms |

Properties of Carrier "A" utilited in Example 1 are the following:

| | |
|---|---|
| Apparent Porosity (%) | 65.6 |
| % Water Absorption | 50.0 |
| Attrition Loss/Hr. (%) | 14.8 |
| 25 Foot Drop Test (% Passing) | 99 |
| Crush Strength Average, lbs. | 20.1 |
| Crush Strength Range, lbs. | 7–29 |
| Surface Area, $M^2/g$. | 0.497 |
| Total Pore Volume (cc/g) | 0.514 |
| Pore Size (Microns) | |
| $P_1$ (<0.1) (%) | 1.5 |
| $P_2$ (0.1–0.5) (%) | 3.0 |
| $P_3$ (0.5–1.0) (%) | 10.0 |
| $P_4$ (1.0–10.0) (%) | 29.0 |
| $P_5$ (10.0–100) (%) | 51.0 |
| $P_6$ (>100) (%) | 5.5 |
| Average O.D. (.320 ± .031) in. | 100 |
| Ratio, Max/Min dia. (% 1.25) | 100 |
| Length, Long Side, %(.346 ± .046) in. | 99 |
| Average Long Side, in. | 0.337 |
| Packing Density, lbs/$ft^3$ | 42.6 |
| Acid Leachable Sodium, ppm. | 903 |
| Acid Leachable Potassium, ppm. | 745 |
| Acid Leachable Calcium, ppm. | 530 |
| Acid Leachable Magnesium, ppm. | 30 |

A. Impregnation Solution Preparation

1. The ethylenediamine was mixed with 50 g distilled water.

2. Oxalic acid was slowly added to the aqueous ethylenediamine solution at ambient conditions. An exothermic reaction occurred and the solution temperature rose to about 40° C.

3. The silver oxide was then added slowly to the solution of step 2.

4. To the solution in 3 above were added the monoethanolamine, the cesium sulfate, and potassium sulfate solutions.

5. Distilled water was added to adjust the solution volume to 250 ml.

B. Impregnation Of Carrier "A"

1 150 grams of Carrier "A" were evacuated at room temperature and the impregnation solution A above was added to Carrier "A" under vacuum.

2. The excess solution was drained off.

C. Catalyst Roasting

1. The impregnation carrier was roasted in hot air using a belt roaster at about 500° C. for 2.5 minutes over a belt roaster. Air flow was 66 SCFH/$in^2$.

2. The finished catalyst contained 13.45 wt. % silver, 0.01957 wt. % cesium and 0.04892 wt. % potassium (as determined by weight picked up by the carrier) as their sulfates.

The catalyst of Example 1 tested at STANDARD ETHYLENE OXIDE PROCESS CONDITIONS under air conditions gave an efficiency of 78.3 percent at 258° C which at oxygen conditions represents an efficiency of 80.6 percent at 235° C. When the above example is repeated using cesium as the hydroxide and potassium as the carbonate, the efficiency in a test at STANDARD ETHYLENE OXIDE PROCESS CONDITIONS and under air conditions was 71.2 percent at 279° C.

If the roast conditions are changed to roasting in a forced air oven at 300° C. for 2 hours, and then tested at STANDARD ETHYLENE OXIDE PROCESS CONDITIONS under air conditions, the catalyst of Example 1 gave an efficiency of 77.0 at 263° C. but when the example is repeated using cesium as the hydroxide and potassium as the carbonate, the catalyst tested at CONDITIONS under air conditions gave no ethylene oxide even at temperatures as high as 294° C. In this comparative illustration, the cesium and potassium are known to be converted by the roast conditions and the oxides of nitrogen from the amine complexing agents into the nitrate salt form (see Nielsen and Schroer, supra).

Example 2

| Ingredients | |
|---|---|
| Carrier "A" | 150 gms |
| Ethylenediamine (High Purity Grade) | 49.62 gms |
| Distilled Water | as indicated |
| Oxalic Acid Dihydrate (Reagent Grade) | 49.70 gms |
| Silver Oxide Power (Metz) | 87.10 gms |
| Monoethanolamine, Fe + Cl free | 17.41 gms |
| Cs Solution as Sulfate (.01473 g Cs/g solution or 0.1474 g Cs) | 10.01 gms |
| K Solution as sulfate (.00544 g K/g solution or 0.0434 g K | 7.97 gms |

A. Solution Preparation

1. The ethylenediamine was mixed with 50 grams of distilled water.

2. Oxalic acid was slowly added to the aqueous ethylenediamine solution at ambient conditions. An exothermic reaction caused the solution temperature to rise to about 40° C.

3. Silver oxide was then added slowly to the above diamine oxalic acid water solution.

4. To the solution 3 above were added the monoethanolamine, the cesium sulfate, and potassium sulfate solutions.

5. Distilled water was added to adjust the solution volume to 250 ml.

B. Impregnation of Carrier "A"

1. 150 grams of Carrier "A" was evacuated at room temperature. The impregnation solution of (A) above was added to Carrier "A" under vacuum.

2. The excess solution was drained off.

C. Catalyst Roasting

The impregnated carrier was roasted in hot air using a belt roaster at about 500° C. for 2.5 minutes over a belt roaster. Air flow was 66.5 SCFH/$in^2$.

2. The finished catalyst contained 13.48 wt. % silver, 0.0240 wt. % cesium and 0.00707 wt. % potassium (as determined by weight picked up by the carrier) as their sulfates.

The catalyst of Example 2 tested at STANDARD ETHYLENE OXIDE PROCESS CONDITIONS under air conditions gave an efficiency of 77.9 percent at 258° C. which at oxygen conditions represents an efficiency of 80.4 percent at 238° C. When the above example is repeated using cesium as the hydroxide and potassium as the carbonate, the efficiency in a test at STANDARD ETHYLENE OXIDE PROCESS CONDITIONS under air conditions was 77.1 percent at 259° C.

Example 3

| Ingredients | |
|---|---|
| Carrier "B" | 65.00 gms |
| Ethylenediamine (High Purity Grade) | 23.70 gms |
| Distilled water | as indicated |
| Oxalic Acid Dihydrate (Reagent Grade) | 23.70 gms |
| Silver Oxide Powder (Metz) | 42.00 gms |
| Monoethanolamine | 8.90 gms |
| Cesium Sulfate Solution | 7.40 gms to provide about 450 ppm Cs on the catalyst. |

A. Solution Preparation

1. The ethylenediamine was mixed with 18.00 grams distilled water.
2. Oxalic acid was slowly added to the aqueous ethylenediamine solution at ambient conditions. An exothermic reaction heated the solution to about 50 60° C.
3. Silver oxide powder was then added slowly to the above diamine-oxalic acid water solution while maintaining temperature below 60° C.
4. Monoethanolamine was added followed by the cesium sulfate solution and enough distilled water to obtain the desired volume (125 ml).

B. Impregnation of Carrier "B"

1 Sixty five grams of Carrier "B" was evacuated (18") at ambient temperature for approximately thirty minutes. Then the impregnating solution obtained in (A) was added to the carrier (maintaining 18" vacuum until carrier was completely covered with solution, then released to atmospheric pressure) and impregnated for one hour.
2. The excess solution was drained off.

C. Catalyst Roasting

1. The impregnated carrier was roasted on the belt roaster at 500° C., for 2.5 minutes in the heating zone with a 66.5 SCFH/in.$^2$ hot air flow blowing upwardly through belt.
2. The finished catalyst contained the following: 13.86 wt. % Ag, 0.0457 wt. % Cs (calculated by wt. gain); 13.63 wt. % Ag, 0.0452 wt. % Cs (by actual analysis).

A series of catalysts were made according to the recipe and procedure of Example 3 except that the amount of cesium sulfate added was adjusted to provide the amounts of cesium set forth in Table I below. Table I records the efficiencies tested at CONDITIONS under air process conditions of catalysts so made. Example 9 describes a catalyst made using cesium hydroxide as the additive. In that case, the cesium hydroxide is converted to the nitrate salt during roasting, thus Example 9 is comparing the nitrate form of cesium to the sulfate form of the other examples.

TABLE I

| | | Air Process Conditions | |
|---|---|---|---|
| Example No. | Cs, ppm | Efficiency, % | Temperature, °C. |
| 4 | 205 | 74.2 | 251.9 |
| 5 | 298 | 76.3 | 256.0 |
| 3 | 457 | 78.0 | 259.9 |
| 6 | 446 | 78.0 | 262.6 |
| 7 | 441 | 77.9 | 259.0 |
| 8 | 441 | 78.9 | 261.0 |
| 9 | *450 | Inactive | 281.0 |
| 10 | 604 | 77.7 | 266.8 |
| 11 | 800 | 77.6 | 270.8 |
| 12 | 994 | 77.2 | 278.2 |
| 13 | 1207 | 75 | 284.9 |

*Added Cs as the hydroxide

These examples demonstrate the great variation in cesium sulfate content one can employ and still obtain extremely effective catalysts. Note the high efficiency coupled with high temperature demonstrating catalysts most suitable for air process conditions where temperature conditions are typically higher than those used under oxygen process conditions.

Example 14

This example shows the addition of cesium and potassium sulfates to the Carrier "B" according to the recipe and procedure of Example 3. In each experiment other than C, listed in Table 11 below, $Cs_2SO_4$ and $K_2SO_4$ were added instead of cesium alone. The catalysts were tested under air conditions according to CONDITIONS and the results in each experiment are set forth in Table II. Experiment C shows what happens when the cesium and potassium were added as their hydroxide and carbonate, respectively.

TABLE II

| Exp. | Cs, ppm | K, ppm | Efficiency, % | Temperature, °C. |
|---|---|---|---|---|
| A. | 195 | 57 | 76.3 | 253.2 |
| B. | 244 | 72 | 76.6 | 258.3 |
| C. | *237 | 60 | Inactive | 281 |
| D | 295 | 86 | 76.9 | 256.9 |
| E. | 355 | 104 | 77.3 | 264.7 |
| F. | 387 | 114 | 75.3 | 274.6 |
| G. | 205 | 514 | 73.2 | 276.6 |
| H. | 230 | 575 | 74.1 | 268.3 |
| I. | 308 | 514 | 75.3 | 269.6 |

*Added Cs and K as the hydroxide and carbonate, respectively.

This example demonstrates the large amounts of cesium and potassium sulfates that can be beneficially used to generate most effective catalysts. It should be appreciated that the catalyst performances characterized in examples 3–14, exclusive of example 9 and experiment C, were not reflective of optimization of catalyst formulation.

Examples 15 through 25

These examples show the addition of different cesium metal salts to the Carrier "C" according to the recipe and procedure of Example 3. Table III below records the efficiencies tested at CONDITIONS under oxygen process conditions of catalysts so made with the exception that the total outlet flow was maintained at 11.3 SCFH and the catalyst volume was 40 cc. It should be appreciated that the catalyst performances characterized in these examples were not reflective of optimization of catalyst formulation.

TABLE III

| Example No. | Cesium Metal Salt | Cs, % Added | Ag, % Added | Efficiency, % | Temperature, °C |
|---|---|---|---|---|---|
| 15 | — | 0 | 13.69 | 73.5 | 238 |
| 16 | cesium chromate ($Cs_2CrO_4$) | 0.0103 | 13.78 | 78.1 | 260 |
| 17 | cesium molybdate ($Cs_2MoO_4$) | 0.0103 | 13.76 | 77.2 | 259 |
| 18 | cesium molybdate ($Cs_2MoO_4$) | 0.0206 | 13.83 | 76.0 | 276 |
| 19 | cesium phosphate ($Cs_3PO_4$) | 0.0200 | 13.41 | 75.9 | 261 |
| 20 | cesium tantalate ($Cs_2Ta_2O_6$) | 0.0311 | 13.89 | 79.1 | 240 |
| 21 | cesium zirconate ($Cs_2ZrO_3$) | 0.0206 | 13.81 | 78.6 | 248 |
| 22 | cesium titanate ($Cs_2TiO_3$) | 0.0306 | 13.65 | 79.2 | 240 |
| 23 | cesium permanganate ($CsMnO_4$) | 0.0101 | 13.55 | 79.7 | 240 |
| 24 | cesium sulfate ($Cs_2SO_4$) | 0.0200 | 13.63 | 78.8 | 248 |
| 25 | cesium vanadate ($Cs_6V_2O_8$) | 0.0103 | 13.79 | 75.0 | 262 |

These examples demonstrate the great variation of oxyanions suitable as counter ions for the alkali metals which can be employed and still obtain extremely effective catalysts.

Examples 26 through 28

These examples demonstrate the addition of cesium and rubidium sulfates to the Carrier "A" according to the recipe and procedure of Example 3. Table IV below records the efficiencies tested at CONDITIONS under air process conditions of catalysts so made. It should be appreciated that the catalyst performances characterized in these examples were not reflective of optimization of catalyst formation.

These examples illustrate the variation of other alkali metal salts which may be employed with cesium salts in the catalysts of this invention.

Examples 29 through 44

These examples demonstrate the addition of various oxyanion salts of cesium and other alkali and alkaline earth metals to various carriers generally according to the recipe and procedure of Example 1. Table V below summarizes the details about the catalyst and the efficiencies at CONDITIONS (oxygen). It should be appreciated that the catalyst performances characterized in these examples were not necessarily reflective of optimization of catalyst formation.

TABLE IV

| Example No. | Silver wt. % | Cs. ppm | Anion | Other Cation Metal | Other Cation Metal ppm | Other Anion Additive | Other Anion, ppm | Carrier | Efficiency % | Temp °C |
|---|---|---|---|---|---|---|---|---|---|---|
| 29 | 13.25 | 92 | $CsMnO_4$ | $KMnO_4$ | 27 | — | — | D | 79.6 | 249 |
| 30[a] | 13.25 | 95 | $CsMnO_4$ | $KMnO_4$ | 28 | $H_2SO_4$ | 48 | D | 76.0 | 254 |
| 31[b] | 13.4 | 301 | $Cs_2Ta_2O_6$ | $K_2SO_4$ | 41 | $H_2SO_4$ | 50 | C | 80.5 | 238 |
| 32[c] | 13.6 | 305 | $Cs_2Ta_2O_6$ | $K_2SO_4$ | 41 | $H_2SO_4$ | 50 | C | 79.6 | 237 |
| 33[d] | 13.0 | 282 | $Cs_2Ti_2O_3$ | $K_2SO_4$ | 38 | $H_2SO_4$ | 47 | D | 80.1 | 251 |
| 34[e] | 14.1 | 51 | $CsMnO_4$ | $KMnO_4$ | 152 | — | — | D | 59.6 | 281 |
| 35[f] | 13.7 | 294 | $Cs_2Ta_2O_6$ | $K_2Ta_2O_6$ | 86 | — | — | D | 74.7 | 265 |
| 36[g] | 17.9 | 280 | $Cs_2MoO_4$ | $K_2SO_4$ | 105 | — | — | H | 77.6 | 267 |
|  |  | 50 | $Cs_2SO_4$ | $Ba(NO_3)$ | 55 |  |  |  |  |  |
| 37[h] | 31 | 355 | $Cs_2Mo_4$ | $Rb_2SO_4$ | 220 | — | — | E | 84.7 | 244 |
|  |  | 190 | $Cs_2SO_4$ |  |  |  |  |  |  |  |
| 38[j] | 16 | 600 | $Cs_2MoO_4$ | $K_2SO_4$ | 450 | — | — | F | 87.9 | 230 |
| 39[k] | 16 | 500 | $Cs_2MoO_4$ | $K_2MoO_4$ | 250 | — | — | G | 81.8 | 256 |
|  |  |  |  | KOH | 250 |  |  |  |  |  |
| 40[l] | 16 | 500 | $Cs_2MoO_4$ | $Ca(NO_3)_2$ | 19 | — | — | H | 84.9 | 230 |
| 41[m] | 16 | 500 | $Cs_2MoO_4$ | $Mg(NO_3)_2$ | 12 | — | — | H | 85.9 | 230 |
| 42[n] | 18 | 250 | $Cs_2MoO_4$ | $K_2MoO_4$ | 250 | — | — |  | 80.4 | 260 |
|  |  |  |  | $K_2SO_4$ | 80 |  |  |  |  |  |
|  |  |  |  | $Ba(NO_3)_2$ | 200 |  |  |  |  |  |
| 43 | 10.5 | 96 | $Cs_2WO_4$ | $K_2CO_3$ | 28 | — | — | I | 69.7 | 263 |
| 44 (comparative) | 10.5 | 96 | CsOH | $K_2CO_3$ | 28 | — | — | I | 69.4 | 258 |

[a] 6.7% $CO_2$
[b] Roasted at 350° C., 15.6 ppm ethyl chloride
[c] 5.0 ppm ethyl chloride, 6.4% $CO_2$
[d] 6.6% $CO_2$
[e] 5 ppm ethyl chloride, 0.2% outlet EO, Air Conditions
[f] 7.0 ppm ethyl chloride
[g] 3.3 ppm ethyl chloride, 1.18% outlet EO Air Conditions
[h] 1.9 ppm ethyl chloride, catalyst prepared using two impregnations with 10 wt % Ag added in the first impregnation.
[j] No $CO_2$, 0.34% outlet EO.
[k] No $CO_2$, 0.4 ppm ethyl chloride, 0.86% outlet EO.
[l] No $CO_2$, 1.0 ppm ethyl chloride, 0.61% outlet EO.
[m] No $CO_2$, 1.0 ppm ethyl chloride, 0.51% outlet EO.
[n] 4% $CO_2$, 4 ppm ethyl chloride.

TABLE IV

| Example No. | Cs, ppm | Rb, ppm | Efficiency % | Temperature °C |
|---|---|---|---|---|
| 26 | 102 | 1017 | 77.3 | 254 |
| 27 | 150 | 1002 | 77.2 | 258 |
| 28 | 101 | 1509 | 77.1 | 260 |

It is claimed:

1. A catalyst for the manufacture of ethylene oxide by the epoxidation of ethylene containing an impregnated silver metal on an inert, refractory solid support and an efficiency-enhancing amount, relative to the amount of silver metal, of a mixture of (i) a cesium salt of an oxyanion of an element selected from Groups 3 through 7b inclusive, of the Periodic Table of the Elements, and (ii) at least one of an alkali metal salt of lithium, sodium, potassium and rubidium and an alkaline earth metal salt, in which the anions of such salts are halides of atomic numbers of 9 to 53, inclusive, and oxyanions of elements other than the oxygen therein having an atomic number of 7 or 15 to 83, inclusive, and selected from Groups 3a to 7a, inclusive, and 3b through 7b, inclusive, of the periodic Table of the Elements.

2. The catalyst of claim 1, wherein the cesium salt (i) is a cesium salt of a titanate, tantalate, molybdate, chromate, zirconate, manqanate or vanadate oxyanion, and the salt (ii) is a lithium, sodium, potassium, rubidium, magnesium, calcium, strontium or barium salt of a manqanate, vanadate, titanate, tantalate, tungstate, molybdate, chromate, zirconate, phosphate or sulfate oxyanion.

3. The catalyst of claim 1, wherein the support is alpha alumina.

4. The catalyst of claim 3 which has been subjected to a process for making ethylene oxide by the reaction of ethylene and oxygen in which a stream comprising ethylene, oxygen, recycled carbon dioxide and a gas phase inhibitor is fed to a fixed bed of said catalyst and ethylene oxide is removed from the fixed bed of said catalyst.

5. The catalyst of claim 3, wherein said catalyst has been subjected to a process for making ethylene oxide at STANDARD ETHYLENE OXIDE PROCESS CONDITIONS under oxygen process conditions.

6. The catalyst of claim 4, wherein said catalyst has been subjected to a process for making ethylene oxide at STANDARD ETHYLENE OXIDE PROCESS CONDITIONS under air process conditions.

7. The catalyst of claim 4, wherein the mixture of metal salts (i) and (ii) is present in an amount, relative to the amount of silver metal, sufficient to provide an efficiency to ethylene oxide manufacture at a value of at least 79 percent, as determined at STANDARD ETHYLENE OXIDE PROCESS CONDITIONS measured under oxygen process conditions.

8. The catalyst of claim 4, wherein the gas phase inhibitor is an organic chloride.

9. The catalyst of claim 4, wherein the stream further comprises ethane.

10. The catalyst of claim 3 which comprises cesium salts and potassium salts.

11. The catalyst of claim 3 which comprises cesium salts and sodium salts.

12. The catalyst of claim 3 which comprises cesium salts and rubidium salts.

13. The catalyst of claim 3 which comprises sulfate anion.

14. The catalyst of claim 13 which comprises at least one of molybdate and tungstate anion.

15. The catalyst of claim 3 which comprises at least one of molybdate and tungstate anion.

16. The catalyst of claim 3 which comprises nitrate anion.

17. The catalyst of claim 3 which comprises as anion, at least one manqanate anion.

18. The catalyst of claim 3 which comprises vanadate.

19. The catalyst of claim 3 which comprises titanate.

20. The catalyst of claim 3 which comprises tantalate.

21. The catalyst of claim 3 which comprises molybdate.

22. The catalyst of claim 3 which comprises chromate.

23. The catalyst of claim 3 which comprises zirconate.

24. The catalyst of claim 3 which comprises tunqstate.

25. A catalyst for the manufacture of ethylene oxide by the epoxidation of ethylene containing an impregnated silver metal on an inert, refractory solid support and an efficiency-enhancing amount, relative to the amount of silver metal, of a mixture of (i) a cesium salt of an oxyanion of an element selected from Groups 3b through 7b inclusive, of the Periodic Table of the Elements; and (ii) an alkali metal salt of lithium, sodium, potassium and rubidium, in which the anions of such salts are oxyanions of elements other than the oxygen therein having an atomic number of 15 or 83 and selected from Groups 3a to 7a, inclusive, and 3b through 7b, inclusive, of the Periodic Table of the Elements.

26. The catalyst of claim 25, wherein the cesium salt (i) is a cesium salt of a titanate, tantalate, molybdate, chromate, zirconate, manganate, tungstate, or vanadate oxyanion, and the alkali metal salt (ii) is a lithium, sodium, potassium, or rubidium salt of a manganate, vanadate, titanate, tantalate, tungstate, molybdate, chromate, zirconate, phosphate or sulfate oxyanion.

27. The catalyst of claim 25, wherein the support is alpha-alumina.

28. The catalyst of claim 27, wherein the catalyst comprises at least one manganate as oxyanion.

29. The catalyst of claim 27, wherein the catalyst comprises vanadate as oxyanion.

30. The catalyst of claim 27, wherein the catalyst comprises titanate as oxyanion.

31. The catalyst of claim 27, wherein the catalyst comprises tantalate.

32. The catalyst of claim 27, wherein the catalyst comprises molybdate.

33. The catalyst of claim 27, wherein the catalyst comprises chromate.

34. The catalyst of claim 27, wherein the catalyst comprises zirconate.

35. The catalyst of claim 27, wherein the catalyst comprises tungstate.

36. The catalyst of claim 27, wherein the catalyst comprises a mixture of cesium and rubidium salts.

37. The catalyst of claim 36, wherein the catalyst contains a molybdate as the oxyanion.

38. The catalyst of claim 27, wherein the catalyst contains a mixture of cesium and potassium salts.

39. The catalyst of claim 36, wherein the catalyst contains molybdate as the oxyanion.

40. The catalyst of claim 36, wherein the catalyst contains tungstate as the oxyanion.

41. A catalyst suitable for the manufacture of ethylene oxide comprising an impregnated silver metal on an inert, refractory solid support and an efficiency-enhancing amount, relative to the amount of silver metal, of a mixture of (i) a cesium salt of an oxyanion of an element other than the oxygen therein selected from Groups 3b through 7b, inclusive, of the Periodic Table of the Elements; and (ii) an alkali metal salt of lithium, sodium, potassium and rubidium, in which the anions of such salts are oxyanions of elements other than the oxygen therein having an atomic number of at least 15 to 83 and being from Groups 3b to 7b, inclusive, and from 3a to 7a, inclusive of the Periodic Table of the Elements, which catalyst has been subjected to a process for making ethylene oxide by the reaction of ethylene and oxygen in which a stream comprising ethylene, oxygen, recycled carbon dioxide and a gas phase inhibitor is fed to a fixed bed of said catalyst and ethylene oxide is removed from the fixed bed of said catalyst.

42. The catalyst of claim 41, wherein the support is alpha-alumina.

43. The catalyst of claim 41 wherein the gas phase inhibitor is an organic chloride.

44. The catalyst of claim 41, wherein the cesium salt (i) is a cesium salt of a titanate, tantalate, molybdate, chromate, zirconate, manqanate or vanadate oxyanion, and the alkali metal salt (ii) is a lithium, sodium, potassium or rubidium salt of a manganate, vanadate, titanate, tantalate, tungstate, molybdate, chromate, zirconate, phosphate or sulfate oxyanion.

* * * * *

UNITED STATES PATENT AND TRADEMARK OFFICE
CERTIFICATE OF CORRECTION

PATENT NO. : 4,908,343
DATED : March 13, 1990
INVENTOR(S) : M.M. Bhasin

It is certified that error appears in the above-identified patent and that said Letters Patent is hereby corrected as shown below:

Column 32:

Claim 1, line 68, "3through" should read --3b through--.

Signed and Sealed this

Twenty-first Day of July, 1992

Attest:

DOUGLAS B. COMER

Attesting Officer

Acting Commissioner of Patents and Trademarks